(12) United States Patent
Fraser et al.

(10) Patent No.: US 7,491,402 B2
(45) Date of Patent: Feb. 17, 2009

(54) SUPERANTIGENS SMEZ-2, SPE-G, SPE-H AND SPE-J AND USES THEREOF

(75) Inventors: John David Fraser, Auckland (NZ); Thomas Proft, Auckland (NZ)

(73) Assignee: Auckland Uniservices Limited, Auckland (NZ)

( * ) Notice: Subject to any disclaimer, the term of this patent is extended or adjusted under 35 U.S.C. 154(b) by 301 days.

(21) Appl. No.: 10/997,690

(22) Filed: Nov. 24, 2004

(65) Prior Publication Data

US 2005/0153376 A1 Jul. 14, 2005

Related U.S. Application Data

(63) Continuation-in-part of application No. 09/869,136, filed as application No. PCT/NZ99/00228 on Dec. 24, 1999, now abandoned.

(30) Foreign Application Priority Data

Dec. 24, 1998 (NZ) .................... 333589

(51) Int. Cl.
*A61K 39/00* (2006.01)
*A61K 39/02* (2006.01)
*A61K 39/38* (2006.01)
*A61K 39/09* (2006.01)
*C07H 21/02* (2006.01)
*G01N 33/53* (2006.01)
*G01N 33/569* (2006.01)
*C07K 1/00* (2006.01)
*C07K 17/00* (2006.01)
*C07K 14/00* (2006.01)

(52) U.S. Cl. ............. 424/237.1; 424/184.1; 424/185.1; 424/190.1; 530/350; 435/7.34; 435/7.1; 536/23.1; 536/23.7; 536/24.32

(58) Field of Classification Search ................. 530/350; 424/184.1, 185.1, 237.1, 190.1; 435/7.34, 435/7.1; 536/23.1, 23.7, 24.32
See application file for complete search history.

(56) References Cited

U.S. PATENT DOCUMENTS

| | | | |
|---|---|---|---|
| 5,545,716 A | 8/1996 | Johnson et al. | |
| 5,698,679 A | 12/1997 | Nemazee | |
| 5,728,388 A | 3/1998 | Terman | |
| 5,858,363 A | 1/1999 | Dohlsten et al. | |
| 5,859,207 A | 1/1999 | Johnson et al. | |
| 5,869,207 A | 2/1999 | Saidi et al. | |
| 5,968,514 A | 10/1999 | Johnson et al. | |
| 6,042,837 A | 3/2000 | Kalland et al. | |
| 6,126,945 A | 10/2000 | Terman et al. | |
| 6,180,097 B1 | 1/2001 | Terman | |
| 6,197,299 B1 | 3/2001 | Dohlsten et al. | |
| 6,221,351 B1 | 4/2001 | Terman | |
| 6,251,385 B1 | 6/2001 | Terman | |
| 6,338,845 B1 | 1/2002 | Terman | |
| 6,340,461 B1 | 1/2002 | Terman | |
| 6,514,498 B1 | 2/2003 | Antonsson et al. | |
| 6,692,746 B1 | 2/2004 | Terman et al. | |
| 7,125,554 B2 * | 10/2006 | Forsberg et al. | 424/183.1 |
| 2003/0039655 A1 * | 2/2003 | Forsberg et al. | 424/178.1 |
| 2003/0092894 A1 | 5/2003 | Antonsson et al. | |
| 2003/0124142 A1 | 7/2003 | Fraser et al. | |
| 2005/0153376 A1 * | 7/2005 | Fraser et al. | 435/7.32 |
| 2006/0160121 A1 * | 7/2006 | Mounts et al. | 435/6 |
| 2006/0210579 A1 * | 9/2006 | Telford et al. | 424/190.1 |
| 2006/0210580 A1 * | 9/2006 | Telford et al. | 424/190.1 |
| 2006/0210581 A1 * | 9/2006 | Telford et al. | 424/190.1 |
| 2006/0210582 A1 * | 9/2006 | Telford et al. | 424/190.1 |
| 2006/0246067 A1 * | 11/2006 | Fraser | 424/144.1 |
| 2006/0258849 A1 * | 11/2006 | Telford et al. | 530/350 |
| 2006/0275315 A1 * | 12/2006 | Telford et al. | 424/190.1 |
| 2007/0082001 A1 * | 4/2007 | Forsberg et al. | 424/155.1 |
| 2007/0092528 A1 * | 4/2007 | Sun | 424/185.1 |

FOREIGN PATENT DOCUMENTS

| | | |
|---|---|---|
| EP | 0 766 566 | 4/2001 |
| WO | 93/14634 | 8/1993 |
| WO | 9/24910 | 6/1998 |
| WO | 98/26747 | 6/1998 |
| WO | 99/27889 | 6/1999 |
| WO | 02/11619 | 2/2002 |
| WO | WO 02/34771 A2 * | 5/2002 |
| WO | 02/45739 | 6/2002 |
| WO | 03/095481 | 11/2003 |
| WO | WO 03/094846 A2 * | 11/2003 |
| WO | 03/101173 | 12/2003 |

OTHER PUBLICATIONS

Yang et al, J. Clinical Microbiology, Jul. 2005, 43/7:3570-3573 abstract only.*
Nooh et al, JBC, Nov. 16, 2006, 281/46:35281-35288.*
Stevens et al, J. Immunology, 1996, 157:2479-2487.*
Baker et al, JBC, 2004, 279/37:38571-38576 abstract only.*
Proft et al, Emerging Infectious Diseases, Oct. 2003, 9/10:1211-1218.*
Banks et al, J. Infectious Diseases, 2004, 190:727-738.*
Hong-Geller et al, J. Molecular Recognition, 2003, 16:91-101.*
Gerlach et al, FEMS Immunology and Medical Microbiology, 2001, 30:209-216.*
Igwe et al, FEMS Microbiology Letters, 2003, 229:259-264.*
Smoot et al, PNAS, Apr. 2, 2002, 99/7:4668-4673.*
Nosoh et al, Protein Stability and Stabilization through protein engineering, 1991, pp. 197-217.*
Protein Structure, a practical approach, T.E. Creighton, 1990, pp. 184-186.*
Burgess et al, JCB, 1990, 111:2129-2138.*
Lazar et al, Molecular and Cellular Biology, 1988, 8:1247-1252.*
Kumar et al, PNAS, 1990, 87:1337-1341.*
Bixler et al, Synthetic Vaccines, 1987, pp. 39-71.*
Bowie et al, Science, Mar. 16, 1990 247:1306-1310.*

(Continued)

*Primary Examiner*—N. M Minnifield
(74) *Attorney, Agent, or Firm*—Occhiuti Rohlicek & Tsao LLP

(57) ABSTRACT

The invention provides superantigens SMEZ-2, SPE-G, SPE-H and SPE-J, as well as polynucleotides which encode them. Such superantigens have, inter alia, diagnostic and therapeutic application.

**

OTHER PUBLICATIONS

Houghten et al, Vaccines86, 1986, pp. 21-25.*
Proteins, T. E. Creighton, 1984, pp. 314-315.*
Stephen C. Goshorn et al. "Nucleotide Sequence of Streptococcal Pyrogenic Exotoxin Type C". Database Swissprot Accession No. P13380. Infection and Immunity 56(9):2518-2520, 1988.
D. Gerlach et al. "Purification and biochemical characterization of a basic superantigen (SPEX/SMEZ3) from *Streptococcus pyogenes*". Database GenPept, Accession No. CAB51744, Jul. 29, 1999.
D. Gerlach et al. "Biochemical purification and characterization of a basic superantigen of *Streptococcus pyogenes*". Database GenPept, Accession No. CAB51332, Jul. 19, 1999.
D. Gerlach et al. "Purification and biochemical characterization of a basic superantigen (SPEX/SMEZ3) from *Streptococcus pyogenes*". Database GenPept, Accession No. CAB51142, Jul. 19, 1999.
Goshorn, et al. "Nucleotide sequence of streptoccal Pyrogenic Exotoxin type C". Database Swiss-Prot, Locus SPEC_STRPY, Accession No. P13380, Jan. 1990.
Goshorn, et al. "Nucleotide sequence of streptococcal Pyrogenic Exotoxin type C". Database GenPept, Accession No. AAB 59091, 1988.
Jodi A. Lindsay et al. "The gene for toxic shock toxin is carried by the family of mobile pathogenicity islands in *Staphylococcus aureus*". Molecular Microbiology 29(2):527-543, 1998.
Vivek Kapur et al. "Molecular Population Genetic Evidence of Horizontal Spread of two Alleles of the Pyrogenic Exotoxin C Gene (speC) among Pathogenic Clones of *Streptococcus pyogenes*". Infection and Immunity 60(9):3513-3517, Sep. 1992.
Sibyl H. Munson et al. "Identification and Characterization of Staphylococcal Enterotoxin Types G and I from *Staphlococcus aureus*". Infection and Immunity 66(7):3337-3348, 1998.
Thomas Proft, et al. "Identification and characterization of novel superantigens from *Streptococcus pyogenes*". Journal of Experimental Medicine 189(1):89-101, 1999.
Thomas Proft, et al. Accession No. AAD52087. "Identification and characterization of novel superantigens from *Streptococcus pyogenes*". Journal of Experimental Medicine 189(1):89-101, 1999.
Alain Roussel et al. "Crystal structure of the streptococcal superantigen SPE-C: dimerization and zinc binding suggest a novel mode of interaction with MHC class II molecules". Nature Structural Biology 4(8):635-643, Aug. 1997.
Thomas Proft, et al. *Superantigens: Just Like Peptides Only Different*. J. Exp. Med. 187(6):819-821, Mar. 1998.

John K. McCormick, et al. *Development of Streptococcal Pyrogenic Exotoxin C Vaccine Toxoids That Are Protective in the Rabbit Model of Toxic Shock Syndrome*. Journal of Immunology, 165:2306-2312, 2000.
Arcus et al. "Conservation and variation in superantigen structure and activity highlighted by the three-dimensional structures of two new superantigens from *Streptococcus pyogens*". J. Molecular Biology 299:157-168, 2000.
Fraser et al. "Superantigens—powerful modifiers of the immune system". Molecular Medicine 6:125-132, Mar. 2000.
Leder et al. "A mutational analysis of the binding of staphylococcal enterotoxins B and C3 to the T cell receptor β chain and major histocompatibility complex class II". J. Exp. Med. 187(6):823-833, Mar. 1998.
Li et al. "Three-dimensional structure of the complex between a T cell receptor β chain and the superantigen staphylococcal enterotoxin B". Immunity 9:807-816, Dec. 1998.
Proft et al. "The streptococcal superantigen SMEZ exhibits wide allelic variation, mosaic structure, and significant antigenic variation". J. Exp. Med. 191(10):1765-1776, May 2000.
Unnikrishnan et al. "The bacterial superantigen streptococcal mitogenic exotoxin Z is the major immunoactive agent of *Streptococcus pyogenes*". The Journal of Immunology 169:2561-2569, 2002.
Thomas Proft, et al. "The Streptococcal Superantigen SMEZ Exhibits Wide Allelic Variation, Mosaic Structure, and Significant Antigenic Variation". J. Exp. Med © The Rockefeller University Press •vol. 191, No. 10, May 15, 2000 1765-1776.
Thomas Proft, et al. "Two Novel Superantigens Found in Both Group A and Group C *Streptococcus*". Infection and Immunity, Mar. 2003, p. 1361-1369.
GenBank, Accession No. AAD52087, Authors: Proft, T, Fleming, N and Fraser JD.
GenBank, Accession No. AAD30988, Authors: Proft, T, Fleming, N and Fraser JD.
GenBank, Accession No. AAL31570, Authors: Proft T, Moffatt, SL, Berkahn, CJ and Fraser, JD.
GenBank, Accession No. AAD30989, Authors: Proft, T, Moffatt, SL, Berkahn, CJ and Frser, JD.
Thomas Proft, et al. "Identification and Characterization of Novel Superantigens from *Streptococcus pyogenes*". J. Exp. Med. © The Rockefeller University Press • vol. 189, No. 1, Jan. 4, 1999 89-101.

* cited by examiner

FIG 1

```
SMEZ    ---------- ---------- LEVDNNSLLR NIVSTIVYEY SDTVIDKLS        30
SMEZ-2  ---------- ---------- LEVDNNSLLR NIVSTIVYEY SDIVIDKLS        30
SPE-J   ---------- ---------- ---------- ---------- ----------
SPE-C   ---------- ------DSKK DISNVKSDLL YATTITPYDY KDCRVNFSYT        34
SPE-G   ---------- --------DE NLKDLKRSLR FATNITPCDY ENVEIAFVTT        32
SPE-H   ---------- ------NSYN TTNREHLESL YKHDSNLIEA DSIKNSPDIV        34
SEA     SEKSEEINE  KDLRKKSELQ GAALGNLKQI YYNEKAKTE  NKESHDQFLQ        49
                                    α2              β1

SMEZ    HNLVTKKLDV RDARDFFINS EMDEYAANDE KDGDKIAMFS VEFDWNYLSE        80
SMEZ-2  HNLVTKKLDV RDARDFFINS EMDEYAANDE KTGDKIAVFS VEFDWNYLSK        80
SPE-J   ---------- ---------- ---------- ---------- LP....YIFT         6
SPE-C   HTLNIDTQKY RG.KDYYISS EMSYEASQKF KRDDVDVFG  LF....YILN        79
SpeG    NSIHINTKQK RSECILYVDS IVSLGITDQF IKGDKVDVEG LE....YNFS        78
SpeH    TS.HML..KY .SVRDKNLSV FFEKDWISQE FKDKEVDIYA LSAQEVCE..        78
SEA     ETILFKGFFT NHSWYNDLLV DFDSKDIVDK YKGKKVDLYG AYYGYQCAGG        99
        β2          β3         α3         β4

SMEZ    GKVIAF.TY GMTPYQEE.. PMSKNIEV  WINRRQIPVE YFQHSTINKTT        127
SMEZ-2  GKVTAF.TY GMTPYQKT.. SILKNDEV  WINGKQISVE YFDHSTINKTT        127
SPE-J   RYDVYF.IY GVTPSVNSN. SENSKIVG  LLDGVQQKTL DFPLKIDKPI         54
SPE-C   SHTGEF.IY GMTPAQN.N. KVNHELLG  FLSGESQQNL NKQILEKDI         126
SPE-G   PPYVDN.IY GMVKHSNQG. NKSLQFVGDL NQDGRETYLE SEAVRIKKKQ        126
SPE-H   CPGKRIEAF GMLTNSEK.. .KEIKVEVV  WDKSKQ..F PMF TVLNPK       124
SEA     TPNKTACMY GVTLHDNNRL TEERVQINLD KQNTVE LETVKTIKKN           149
                 β5          β6          β7          β8

SMEZ    VTAQEIDLKV KFLISQHQL  SSGSSYKSG KLVFHTNDNS DKYSLDIFYV        177
SMEZ-2  VTAQEIDLKV KFLIAQEQL  SSGSSYKSG RLVFHTNDNS DKYSFDIFYV        177
SPE-J   FTIQEFDFKI QYFMQTYKI  DPNSPYIKG QLEIAINGNK .HESFNLYDA        103
SPE-C   VLFQEDDFKI KYLMDNYKI  DATSPIWSG RIEIGTKDGK .HEQIDIFDS        175
SPE-G   FTLQEFDFKI KFLMEKYNI  DSESRYTSG SLFLAKDSK  .HYEVDIFNK        175
SPE-H   VTAQEVDIKV KLIIKKYDI  NNR..EQKY SKGTVLLDLN SGKDIVFDLY        172
SEA     VTVQELDLQA RYLQEKYNL  NSDVFDGKV QRGLIVFHTS TEPSVNYDLF        199
        β8    α4                         β9         β10

SMEZ    ..GYRDKESI ERVVKI HSF  IIDKIGHLDL EIDS       209
SMEZ-2  ..GYRDKESI ERVVKI HSF  IIDKIGHLDL EIDS       209
SPE-J   TSS.STRSDI FKKVKI KTI  MKDFSHFDI  YIWTK      137
SPE-C   PNE.GTRSDI EAKVKI RII  MKNFSHFDI  YIEK       208
SPE-G   DDKLLSRDSF FKKVKI KIF  SEEISHFDI  YIKTH      210
SPE-H   YFGNGDFNSM LIDSN  ERI  DSTQF.EVDV SIS        204
SEA     GAQGQNSNTL LRIRRI KTI  NSENM.HIDI YLYTS      233
             α5       β11     β12
```

FIG 2

```
         10                    30                    50
         .                     .                     .
ATGAAAAAAACAAAACTTATTTTTTCTTTTACTTCAATATTCATTGCAATAATTTCTCGT
 M  K  K  T  K  L  I  F  S  F  T  S  I  F  I  A  I  I  S  R 70                    90                   110
         .                     .                     .
CCTGTGTTTGGATTAGAAGTAGATAATAATTCCCTTCTAAGGAATATCTATAGTACGATT
 P  V  F  G  L  E  V  D  N  N  S  L  L  R  N  I  Y  S  T  I 130                   150                   170
         .                     .                     .
GTATATGAATATTCAGATATAGTAATTGATTTTAAAACCAGTCATAACTTAGTGACTAAG
 V  Y  E  Y  S  D  I  V  I  D  F  K  T  S  H  N  L  V  T  K 190                   210                   230
         .                     .                     .
AAACTTGATGTTAGAGATGCTAGAGATTTCTTTATTAACTCCGAAATGGACGAATATGCA
 K  L  D  V  R  D  A  R  D  F  F  I  N  S  E  M  D  E  Y  A 250                   270                   290
         .                     .                     .
GCCAATGATTTTAAAACTGGAGATAAAATAGCTGTGTTCTCCGTCCCATTTGATTGGAAC
 A  N  D  F  K  T  G  D  K  I  A  V  F  S  V  P  F  D  W  N 310                   330                   350
         .                     .                     .
TATTTATCAAAAGGAAAAGTCACAGCATATACCTATGGTGGAATAACACCCTACCAAAAA
 Y  L  S  K  G  K  V  T  A  Y  T  Y  G  G  I  T  P  Y  Q  K 370                   390                   410
         .                     .                     .
ACTTCAATACCTAAAAAtatCCCTGTTAATTTATGGattaatGgAAAGcagatCTCTgtT
 T  S  I  P  K  N  I  P  V  N  L  W  I  N  G  K  Q  I  S  V 430                   450                   470
         .                     .                     .
CcTtaCaaCGAAATATCaaCTAACAAAACAacaGTTACAGCTCAAGAAAttgATCTAAAG
 P  Y  N  E  I  S  T  N  K  T  T  V  T  A  Q  E  I  D  L  K 490                   510                   530
         .                     .                     .
GTTAGAAAATTTTTAATAGCACAACATCAATTATATTCTTCTGGTTCTAGCTACAAAAGT
 V  R  K  F  L  I  A  Q  H  Q  L  Y  S  S  G  S  S  Y  K  S 550                   570                   590
         .                     .                     .
GGTAGACTGGTTTTTCATACAAATGATAATTCAGATAAATATTCTTTCgatcTTTTctat
 G  R  L  V  F  H  T  N  D  N  S  D  K  Y  S  F  D  L  F  Y 610                   630                   650
         .                     .                     .
gtagGATATAGAGATAAAGAAAGTATCTTTAAAGTATACAAAGACAATAAATCTTTCAAT
 V  G  Y  R  D  K  E  S  I  F  K  V  Y  K  D  N  K  S  F  N 670                   690
         .                     .
ATAGATAAAATTGGGCATTTAGATATAGAAATTGACTCCTAA
 I  D  K  I  G  H  L  D  I  E  I  D  S  *
```

FIG 3

```
        10                    30                    50
         .                     .                     .
ATGAAAACAAACATTTTGACAATTATCATATTATCATGTGTTTTAGCTATGGAAGTCAA
 M  K  T  N  I  L  T  I  I  I  L  S  C  V  F  S  Y  G  S  Q 70                    90                   110
         .                     .                     .
TTAGCTTATGCAGATGAAAATTTAAAAGATTTAAAAAGAAGTTTAAGATTTGCCTATAAT
 L  A  Y  A  D  E  N  L  K  D  L  K  R  S  L  R  F  A  Y  N 130                   150                   170
         .                     .                     .
ATTACCCCATGCGATTATGAAAATGTAGAAATTGCATTTGTTACTACAAATAGCATACAT
 I  T  P  C  D  Y  E  N  V  E  I  A  F  V  T  T  N  S  I  H 190                   210                   230
         .                     .                     .
ATTAATACTAAACAAAAAGATCGGAATGTATTCTTTATGTTGATTCTATTGTATCTTTA
 I  N  T  K  Q  K  R  S  E  C  I  L  Y  V  D  S  I  V  S  L 250                   270                   290
         .                     .                     .
GGCATTACTGATCAGTTTATAAAAGGGGATAAGGTCGATGTTTTTGGTCTCCCTTATAAT
 G  I  T  D  Q  F  I  K  G  D  K  V  D  V  F  G  L  P  Y  N 310                   330                   350
         .                     .                     .
TTTTCCCCACCTTATGTAGATAATATTTATGGTGGTATTGTAAAACATTCGAATCAAGGA
 F  S  P  P  Y  V  D  N  I  Y  G  G  I  V  K  H  S  N  Q  G 370                   390                   410
         .                     .                     .
AATAAATCATTACAGTTTGTAGGAATTTTAAATCAAGATGGGAAAGAAACTTATTTGCCC
 N  K  S  L  Q  F  V  G  I  L  N  Q  D  G  K  E  T  Y  L  P 430                   450                   470
         .                     .                     .
TctgAGGCTGTTCGCATAAAAAAGAAACAGTTTACTTTACAGGAATttgATTTTAAAATA
 S  E  A  V  R  I  K  K  K  Q  F  T  L  Q  E  F  D  F  K  I 490                   510                   530
         .                     .                     .
AGAAAATTTCTAATGGAAAAATACAATATCTATGATTCGGAATCGCGTTATACATCGGGG
 R  K  F  L  M  E  K  Y  N  I  Y  D  S  E  S  R  Y  T  S  G 550                   570                   590
         .                     .                     .
AGCCTTTTCCTTGCTACTAAAGATAGTAAACATTATGAAGTTGATTTATTTAATAAGGAT
 S  L  F  L  A  T  K  D  S  K  H  Y  E  V  D  L  F  N  K  D 610                   630                   650
         .                     .                     .
GATAAGCTTTTAAGTCGAGACAGTTTCTTTAAAAGGTATAAAGATAATAAGATTTTTAAT
 D  K  L  L  S  R  D  S  F  F  K  R  Y  K  D  N  K  I  F  N 670                   690
         .                     .
AGTGAAGAAATTAGTCATTTTGATATCTACTTAAAAACGCACTAG
 S  E  E  I  S  H  F  D  I  Y  L  K  T  H  *
```

FIG 4

```
          10                    30                    50
           .                     .                     .
ATGAGATATAATTGTCGCTACTCACATATTGATAAGAAAATCTACAGCATGATTATATGT
 M  R  Y  N  C  R  Y  S  H  I  D  K  K  I  Y  S  M  I  I  C 70                    90                   110
           .                     .                     .
TTGTCATTTCTTTTATATTCCAATGTTGTTCAAGCAAATTCTTATAATACAACCAATAGA
 L  S  F  L  L  Y  S  N  V  V  Q  A  N  S  Y  N  T  T  N  R 130                   150                   170
           .                     .                     .
CATAATCTAGAATCGCTTTATAAGCATGATTCTAACTTGATTGAAGCCGATAGTATAAAA
 H  N  L  E  S  L  Y  K  H  D  S  N  L  I  E  A  D  S  I  K 190                   210                   230
           .                     .                     .
AATTCTCCAGATATTGTAACAAGCCATATGTTGAAATATAGTGTCAAGGATAAAAATTTG
 N  S  P  D  I  V  T  S  H  M  L  K  Y  S  V  K  D  K  N  L 250                   270                   290
           .                     .                     .
TCAGTTTTTTTTGAGAAAGATTGGATATCACAGGAATTCAAAGATAAAGAAGTAGATATT
 S  V  F  F  E  K  D  W  I  S  Q  E  F  K  D  K  E  V  D  I 310                   330                   350
           .                     .                     .
TATGCTCTATCTGCACAAGAGGTTTGTGAATGTCCAGGGAAAAGGTATGAAGCGTTtggt
 Y  A  L  S  A  Q  E  V  C  E  C  P  G  K  R  Y  E  A  F  G 370                   390                   410
           .                     .                     .
GGAATTACATTAACTAATTCAGAAAAAAAAGAAATTAAAGTTCCTGTAAACGtgtGggat
 G  I  T  L  T  N  S  E  K  K  E  I  K  V  P  V  N  V  W  D 430                   450                   470
           .                     .                     .
AAAAGTAAACAACAGCCGCCTATGTTTATTACAGTCAATAAACCGAAAgtaaCCGCTCAG
 K  S  K  Q  Q  P  P  M  F  I  T  V  N  K  P  K  V  T  A  Q 490                   510                   530
           .                     .                     .
GAAGTGGATATAAAAGTTAGAAAGTTATTGAttaagaaatacgATATCTATAATAaccgg
 E  V  D  I  K  V  R  K  L  L  I  K  K  Y  D  I  Y  N  N  R 550                   570                   590
           .                     .                     .
gaacaaaaatactctaaaggaactgttaccttagATTTAAATTCAGGTAAAGATATTGTT
 E  Q  K  Y  S  K  G  T  V  T  L  D  L  N  S  G  K  D  I  V 610                   630                   650
           .                     .                     .
TTTGATTTGTATTATTTTGGCAATGGAGACTTTAATAGCATGCTAAAAATATATTCCAAT
 F  D  L  Y  Y  F  G  N  G  D  F  N  S  M  L  K  I  Y  S  N 670                   690                   710
           .                     .                     .
AACGAGAGAATAGactcaactCAATTTCATGTAGatgTGTCaatcagctaA
 N  E  R  I  D  S  T  Q  F  H  V  D  V  S  I  S  *
```

FIG 5

```
          10                    30                    50
           .                     .                     .
CTTCCGTACATATTTACTCGTTATGATGTTTATTATATATATGGTGGGGTTACACCATCA
 L  P  Y  I  F  T  R  Y  D  V  Y  Y  I  Y  G  G  V  T  P  S 70                    90                   110
           .                     .                     .
GTAAACAGTAATTCGGAAAATAGTAAAATTGTAGGTAATTTACTAATAGATGGAGTCCAG
 V  N  S  N  S  E  N  S  K  I  V  G  N  L  L  I  D  G  V  Q 130                   150                   170
           .                     .                     .
CAAAAAACACTAATAAATCCCATAAAAATAGATAAACCTATTTTTACGATTCAAGAATTT
 Q  K  T  L  I  N  P  I  K  I  D  K  P  I  F  T  I  Q  E  F 190                   210                   230
           .                     .                     .
GACTTCAAAATCAGACAATATCTTATGCAAACATACAAAATTTATGATCCTAATTCTCCA
 D  F  K  I  R  Q  Y  L  M  Q  T  Y  K  I  Y  D  P  N  S  P 250                   270                   290
           .                     .                     .
TACATAAAAGGGCAATTAGAAATTGCGATCAATGGcaATAAACATGAAAGTTTTAACTTA
 Y  I  K  G  Q  L  E  I  A  I  N  G  N  K  H  E  S  F  N  L 310                   330                   350
           .                     .                     .
TATGATGCAACCTCATCTAGTACAAGGAGTGATATTTTTAAAAAATATAAAGACaATAAG
 Y  D  A  T  S  S  S  T  R  S  D  I  F  K  K  Y  K  D  N  K 370                   390                   410
           .                     .                     .
ACTATAAATATGAAAGATTTCAGCCATTTTGATATTTACCTTtggACTAAATAA
 T  I  N  M  K  D  F  S  H  F  D  I  Y  L  W  T  K  *
```

FIG 6
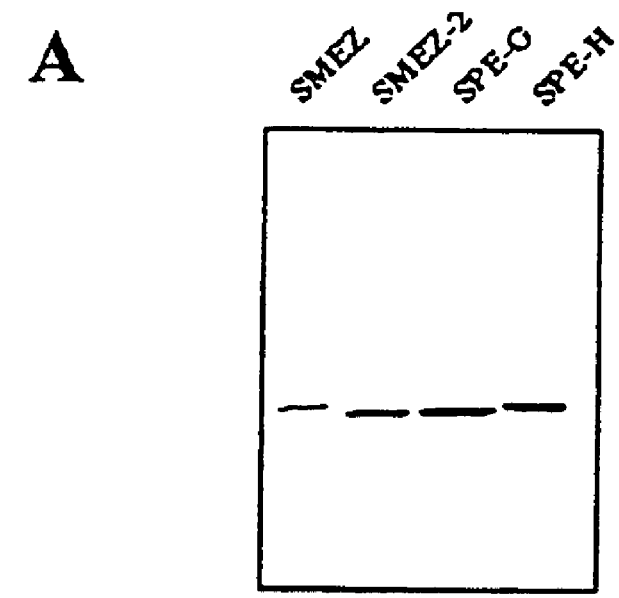
A
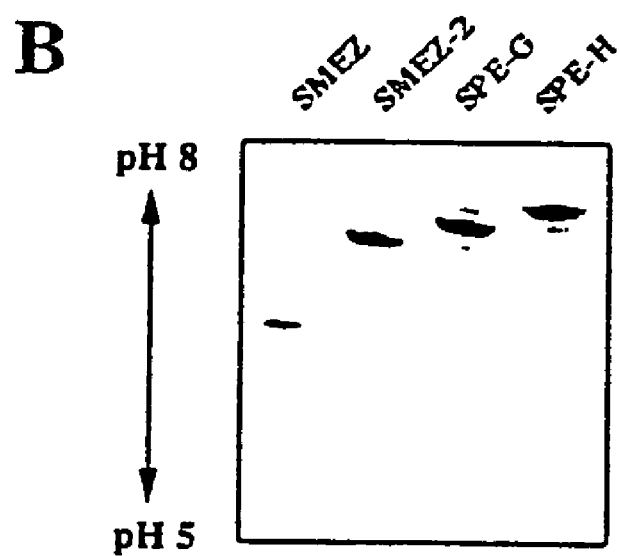
B

SUPERANTIGENS SMEZ-2, SPE-G, SPE-H AND SPE-J AND USES THEREOF

RELATED APPLICATIONS

This application is a continuation-in-part application of and claims priority to U.S. application Ser. No. 09/869,136 filed Jul. 20, 2001, now abandoned which is a U.S. national phase application of and claims priority to International Application Number: PCT/NZ99/00228 filed Dec. 24, 1999, the contents of which are incorporated herein by reference.

TECHNICAL FIELD

This invention relates to superantigens, and to their use, including in diagnosis and/or treatment of disease.

BACKGROUND ART

Bacterial superantigens are the most potent T cell mitogens known. They stimulate large numbers of T cells by directly binding to the side of the MHC class II and T cell Receptor (TcR) molecules. Because they override the normally exquisite MHC restriction phenomenon of T cell antigen recognition, they are prime candidates for either causing the onset of autoimmune diseases or exacerbating an existing autoimmune disorder.

The applicants have identified genes coding for four novel superantigens from *S. pyogenes*. It is broadly to these superantigens and polynucleotides encoding them that the present invention is directed.

SUMMARY OF THE INVENTION

In one aspect, the invention provides a superantigen selected from any one of SMEZ-2, SPE-G, SPE-H and SPE-J, or a functionally equivalent variants thereof. All functionally equivalent variants of SMEZ-2 contain the sequence of KTSIP (SEQ ID NO:25).

In a further aspect the invention provides a polynucleotide molecule comprising a sequence encoding a superantigen chosen from SMEZ-2, SPE-G, SPE-H, SPE-J, or a functionally equivalent variant thereof.

In another aspect of the invention there is provided a method of subtyping *Streptococci* on the basis of superantigen genotype comprising detection of the presence of any or all of the above four superantigens or the corresponding polynucleotides.

In a further aspect the invention provides a construct comprising any of the above superantigens (or superantigen variants) bound to a cell-targeting molecule, which is preferably a tumour-specific antibody.

In yet a further aspect, the invention provides a pharmaceutical composition for therapy or prophylaxis comprising a superantigen or superantigen variant as described above linked to cell targeting molecule.

Other aspects of the invention will be apparent from the description provided below, and from the appended claims.

DESCRIPTION OF DRAWINGS

While the invention is broadly defined above, it further includes embodiments of which the following description provides examples. It will also be better understood with reference to the following drawings:

FIG. 1: Multiple alignment of superantigen protein sequences (SEQ ID NOs:9, 20, 8, 10, 21, 22 and 11, respectively, in order of appearance).

The protein sequence of mature toxin, i.e., SMEZ (SEQ ID NO:9), SMEZ-2 (SEQ ID NO:20), SPE-J (SEQ ID NO:8), SPE-C (SEQ ID NO:10), SPE-G (SEQ ID NO:21), SPE-H (SEQ ID NO:22), and SEA (SEQ ID NO: 11), were aligned using the PileUp programme on the GCG package. Regions of high sequence identity are in black boxes. The boxes below the sequences indicate the structural elements of SPE-C, as determined from the crystal structure (Roussel et al 1997 Nat. Struct. Biol. 4 no8:635-43). Regions with highest homology correspond to the $\beta4$, $\beta5$, $\alpha4$ and $\alpha5$ regions in SPE-C. The clear box near the C-terminus represents a primary zinc binding motif, a common feature of all toxins shown. The arrows on top of the sequence alignment show the regions of sequence diversity between SMEZ and SMEZ-2.

FIG. 2: The nucleotide sequence of the portion of the smez-2 gene (SEQ ID NO. 1) coding the precursor SMEZ-2 superantigen (SEQ ID NO. 2).

FIG. 3: The nucleotide sequence of the portion of the spe-g gene (SEQ ID NO. 3) coding the precursor SPE-G superantigen (SEQ ID NO. 4).

FIG. 4: The nucleotide sequence of the portion of the spe-h gene (SEQ ID NO. 5) coding the precursor SPE-H superantigen (SEQ ID NO. 6).

FIG. 5: The nucleotide sequence of the portion of the spe-j gene (SEQ ID NO. 7) coding part of the mature SPE-J superantigen (SEQ ID NO. 8).

FIG. 6: Gel electrophoresis of the purified recombinant toxins.

A. Two micrograms of purified recombinant toxin were run on a 12.5% SDS-polyacrylamide gel to show the purity of the preparations; B. Two micrograms of purified recombinant toxin were run on an isoelectric focusing gel (5.5% PAA, pH 5-8). The isoelectric point (IEP) of rSMEZ-2, rSPE-G and rSPE-H is similar and was estimated at pH 7-8. The IEP of rSMEZ was estimated at pH 6-6.5.

Figure 7:
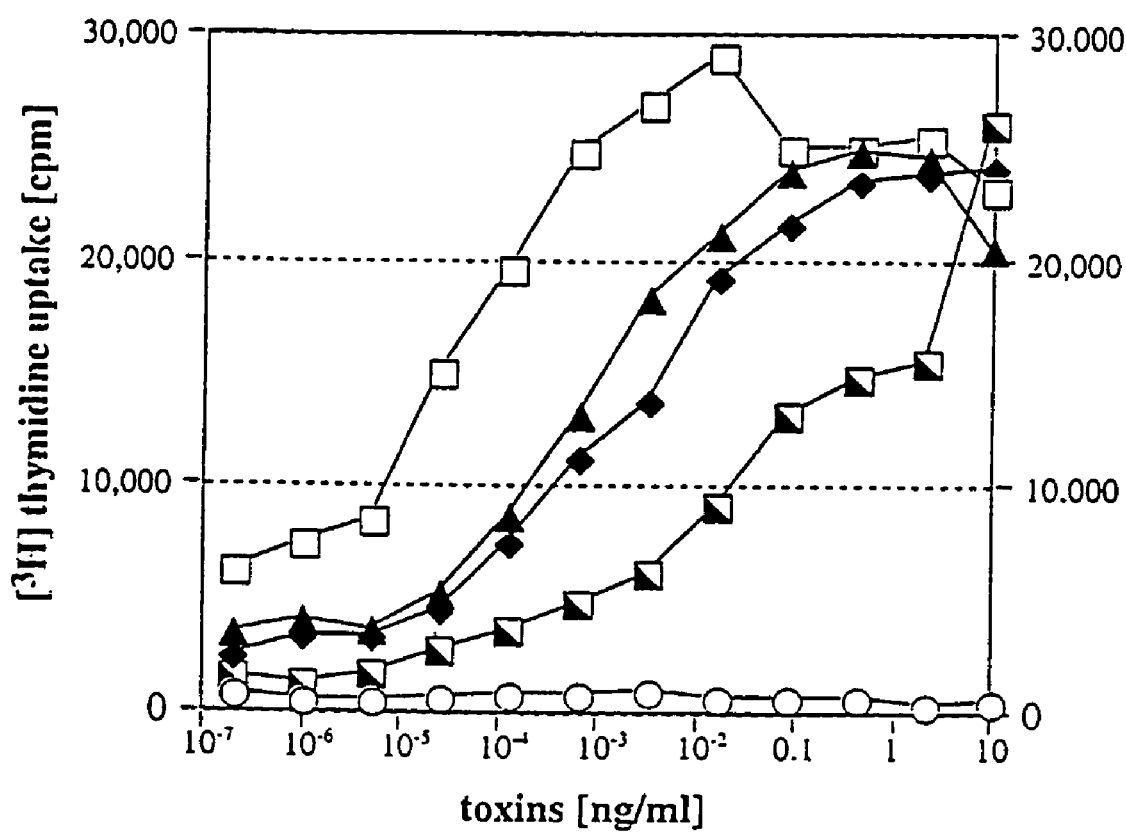

FIG. 7: Stimulation of human T cells with recombinant toxins.

PBLs were isolated from human blood samples and incubated with varying concentrations of recombinant toxin. After 3 d, 0.1 µCi [$^3$H]-thymidine was added and cells were incubated for another 24 h, before harvested and counted on a gamma counter. ○, unstimulated; ▲, rSMEZ; ⨅, rSMEZ-2; ◆, rSPE-G; ◨, rSPE-H.

Figure 8:
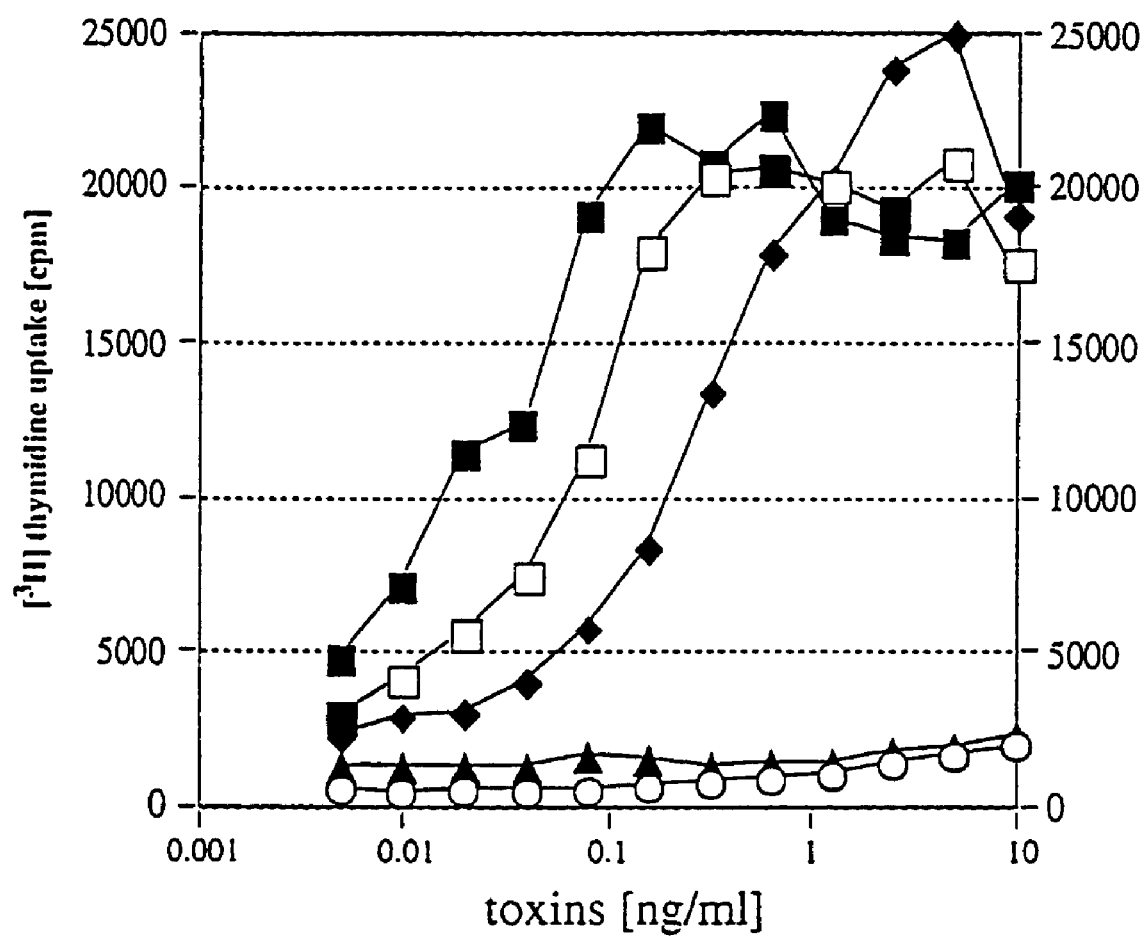

FIG. 8: Jurkat cell assay

Jurkat cells (bearing a V$\beta$8 TcR) and LG-2 cells were mixed with varying concentrations of recombinant toxin and incubated for 24 h, before Sel cells were added. After 1 d, 0.1 µCi [$^3$H]-thymidine was added and cells were counted after another 24 h. The V$\beta$8 targeting SEE was used as a positive control. The negative control was SEA. Both SMEZ and SMEZ-2 were potent stimulators of Jurkat cells, indicating their ability to specifically target V$\beta$8 bearing T cells. ○, unstimulated; ▲, rSEA; ⨅, rSEE; ◆, rSMEZ; ■, rSMEZ-2.

Figure 9:
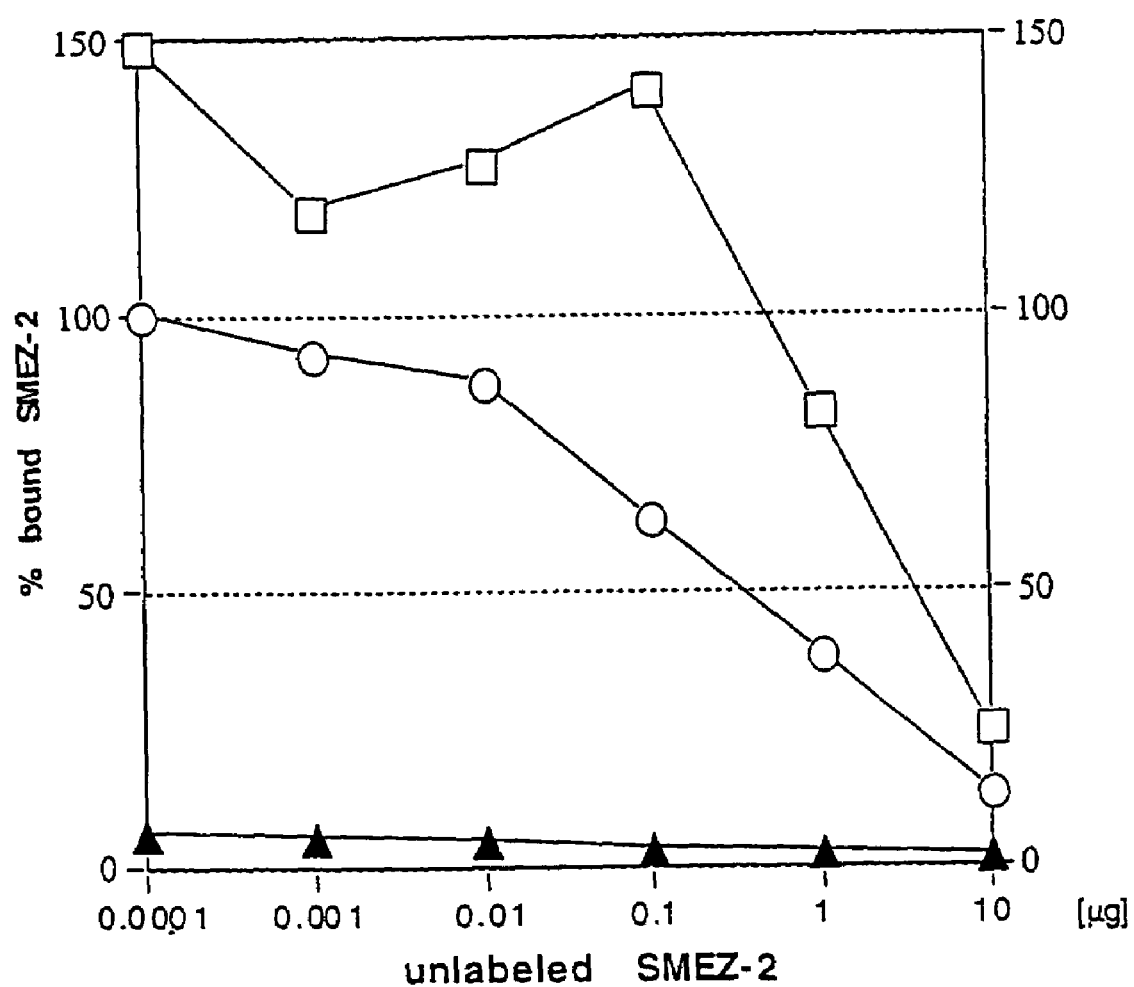

FIG. 9: Zinc dependent binding of SMEZ-2 to LG-2 cells

LG-2 cells were incubated in duplicates with 1 ng of $^{125}$I labelled rSMEZ-2 and increasing amounts of unlabeled toxin at 37° C. for 1 h, and then the cells were washed and counted.

○, incubation in media; ◆, incubation in media plus 1 mM EDTA; ⨅, incubation in media plus 1 mM EDTA, 2 mM $ZnCl_2$.

Figure 10:
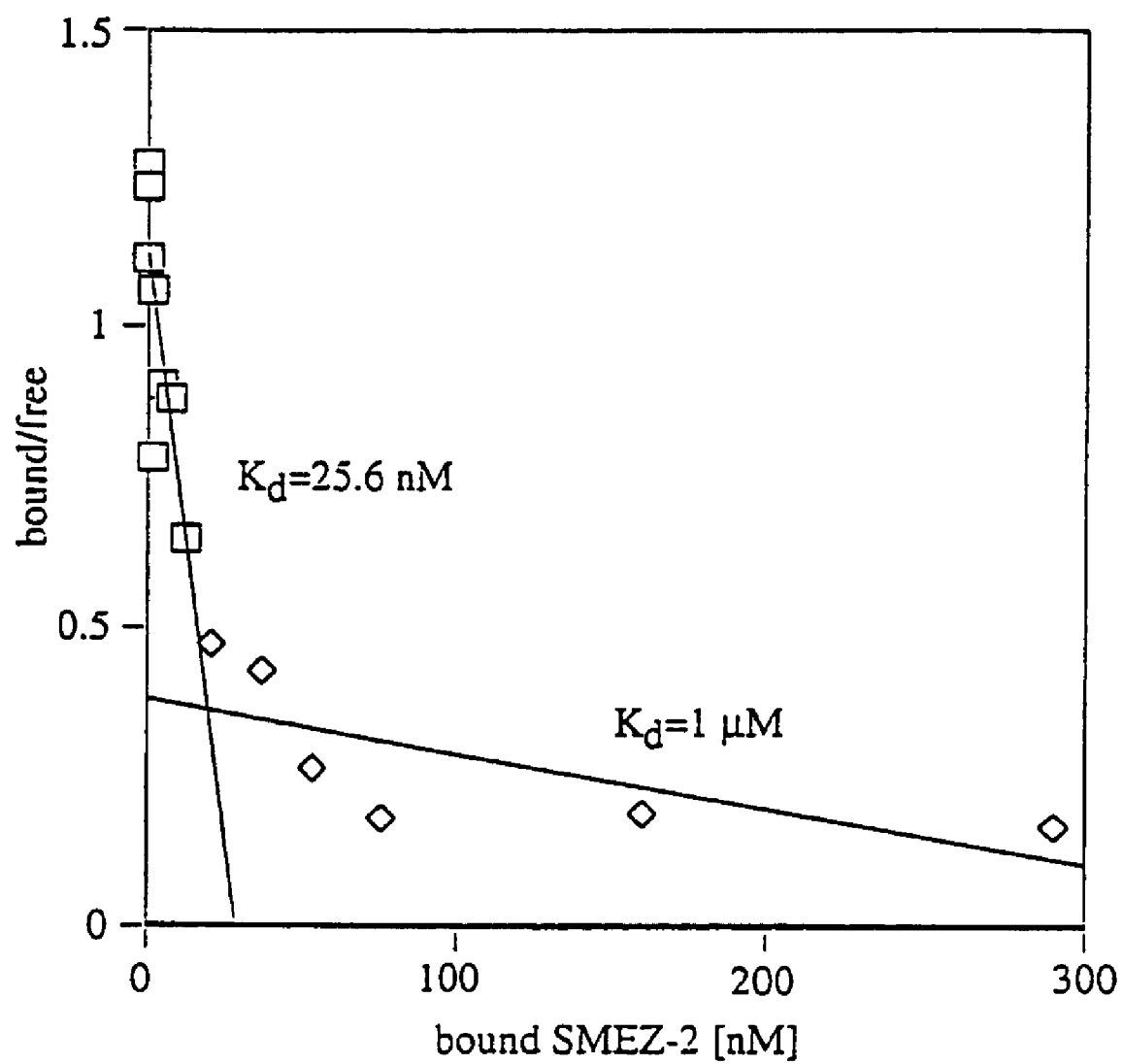

FIG. 10: Scatchard analysis of SMEZ-2 binding to LG-2 cells

One nanogram $^{125}$I-labeled rSMEZ-2 was incubated in duplicates with LG-2 cells and a 2-fold dilution series of cold toxin (10 μg to 10 μg). After 1 h, cells were washed and counted. Scatchard plots were performed as described by Cunningham et al 1989 Science 243:1330-1336.

Figure 11:
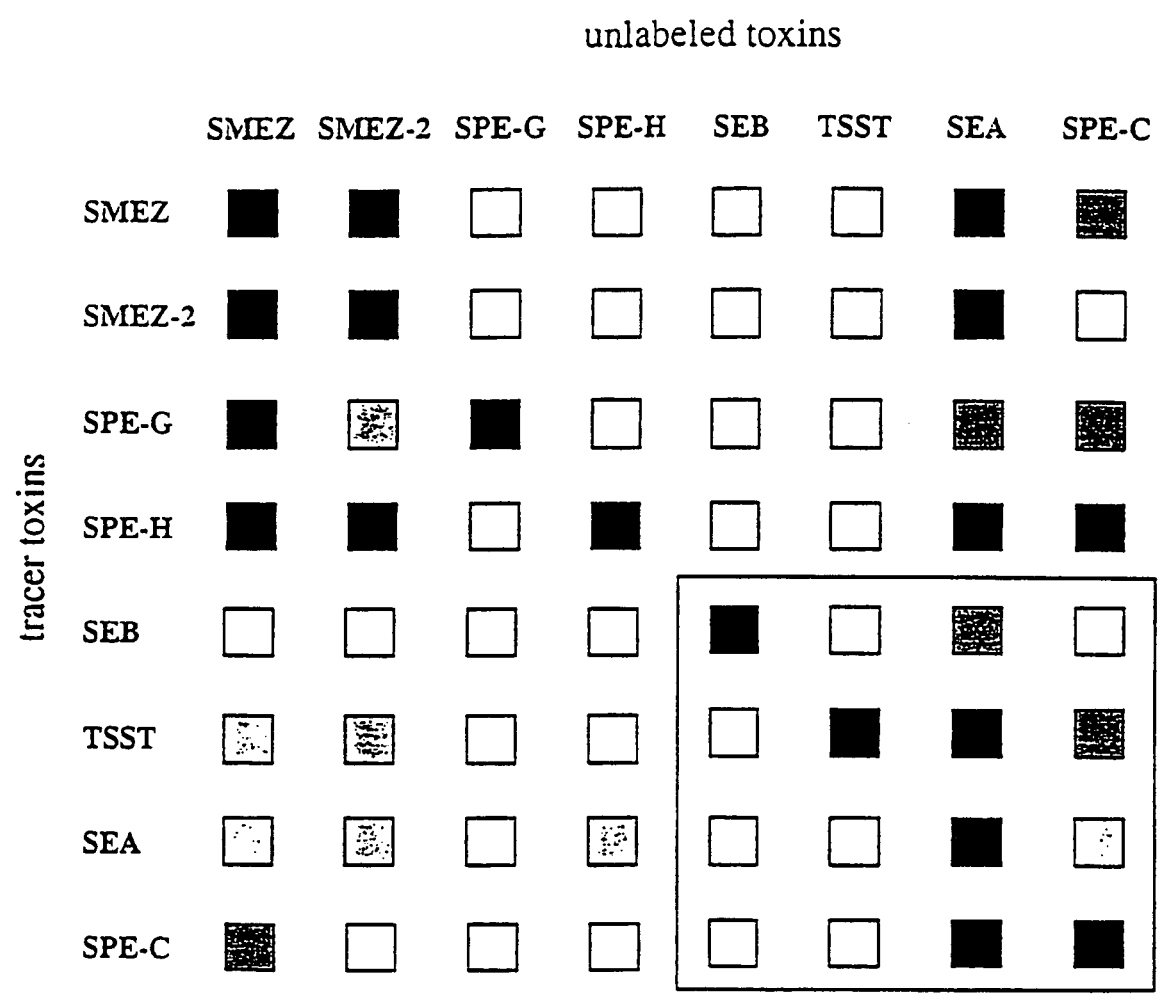

FIG. 11: Summary of competitive binding experiments.

Efficiency of each labelled toxin to compete with a 10,000-fold molar excess of any other unlabeled toxin for binding to LG-2 cells. □, no competition; ▨, 25% competition; ▩, 50% competition; ▨75% competition; ■, 100% competition. The results within the boxes are at the bottom right have previously been published (Li et al. 1997).

Figure 12:
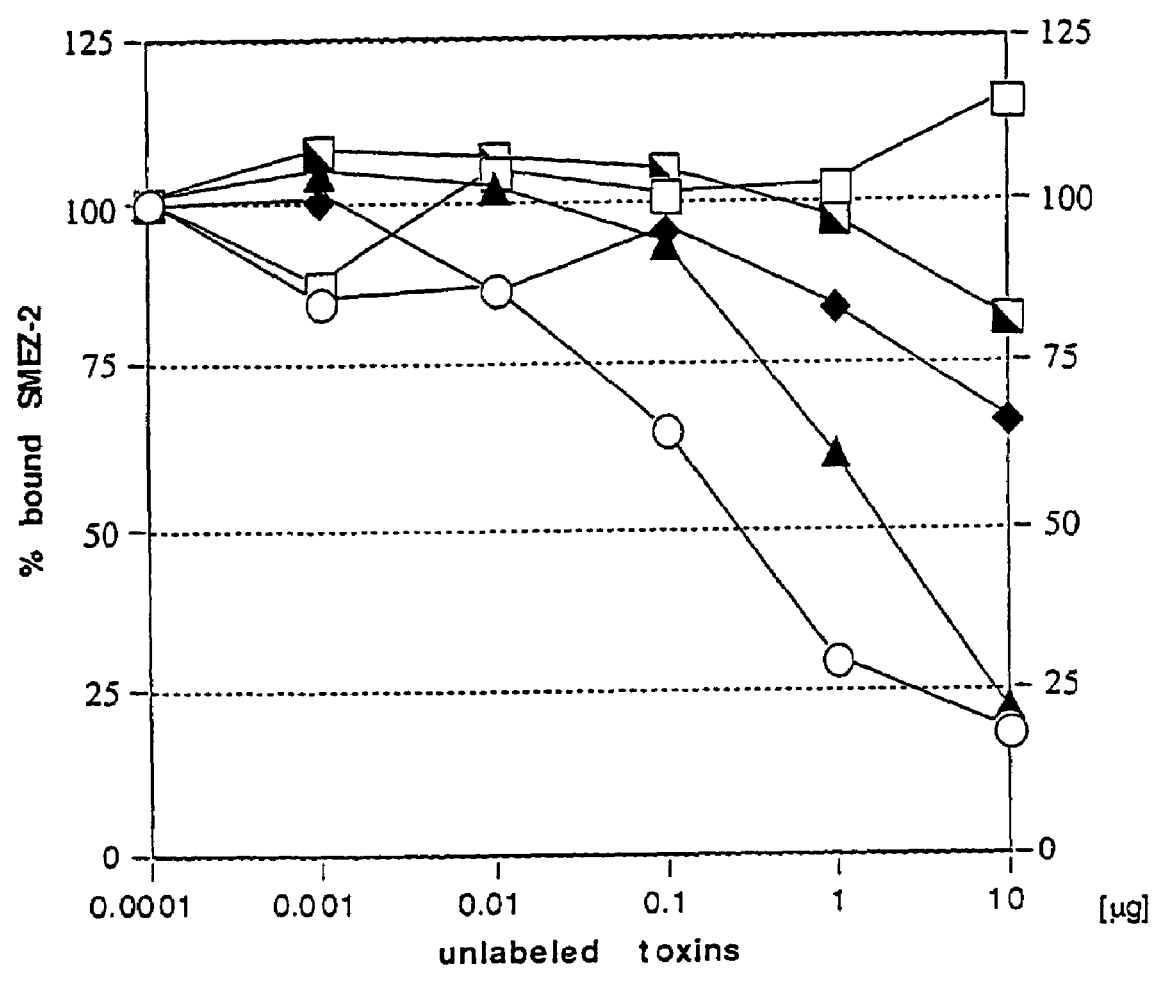

FIG. 12: Competition binding study with SMEZ-2.

LG-2 cells were incubated in duplicates with 1 ng of $^{125}$I-labeled rSMEZ-2 and increasing amounts of unlabeled rSMEZ-2, rSEA, rSEB, rTSST or rSPE-C. After 1 h cells were washed and counted.

○, rSMEZ-2; ▲, rSEA; Z, rSEB; ▪rTSST; ♦, rSPE-C.

Figure 13:
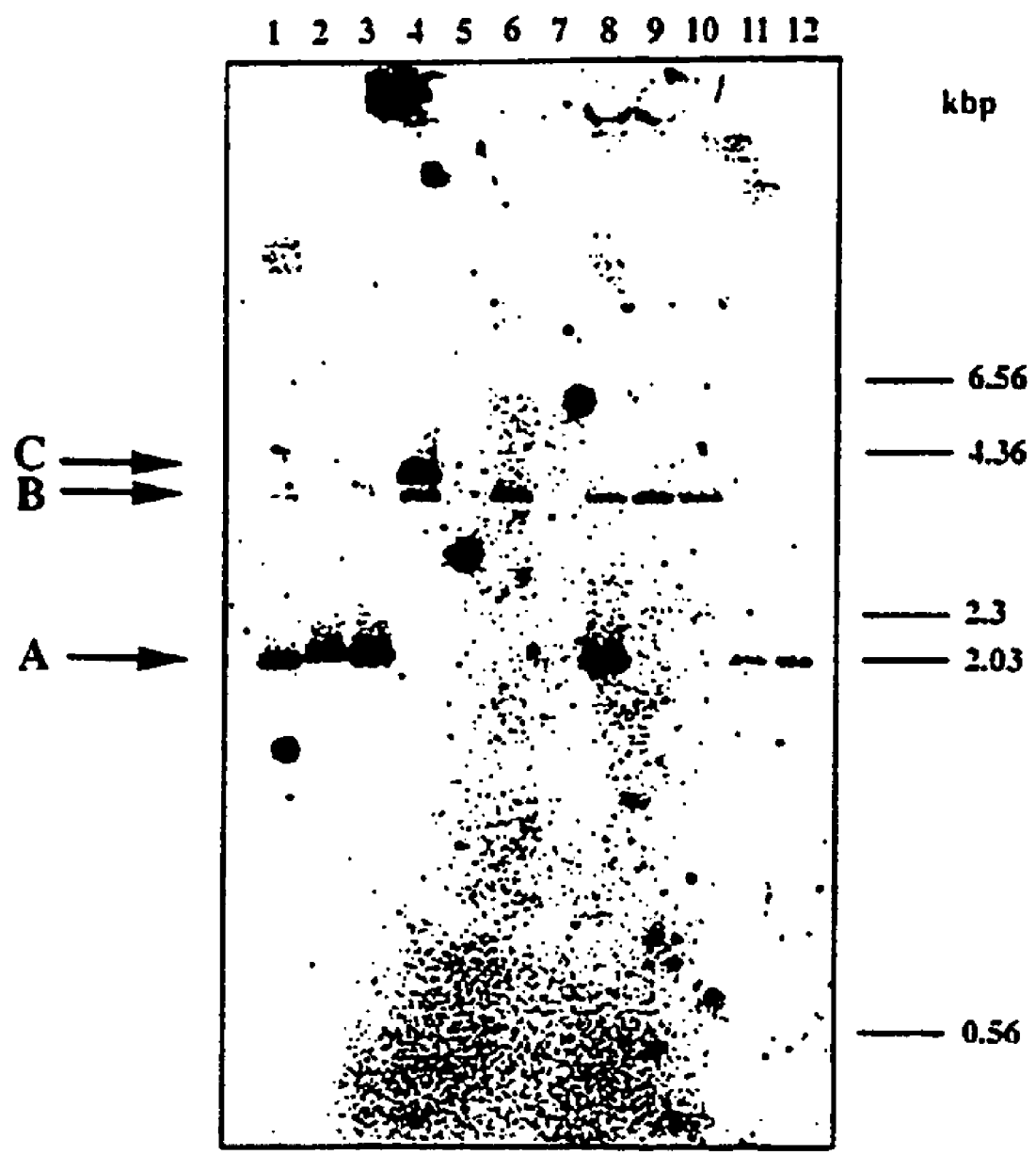

FIG. 13: Southern blot analysis of genomic DNA with radiolabeled smez. HINDIII digested genomic DNA from various *Steptococcus* isolates was hybridized with a radiolabeled smez probe. Band A is a 1953 bp HindIII DNA fragment that carries the smez gene. Bands B and C are DNA fragments of about 4 kbp and 4.2 kbp, respectively, which both carry a smez like region. 1, *S. pyogenes* reference strain (ATCC 700294, M1 type); 2, isolate 9639 (MNT); 3, isolate 11789 (MNT); 4, isolate 11152 (PT2612 type); 5, isolate RC4063 (group C *streptococcus*); 6, isolate 11070 (emm65 type); 7, DNA marker lane; 8, isolate 4202 (NZ5118/M92 type); 9, isolate 94/229 (M49 type); 10, isolate 11610 (emm57 type); 11, isolate 95/127 (NZ1437/M89 type); 12, isolate 94/330 (M4 type).

DESCRIPTION OF THE INVENTION

The focus of the invention is the identification of four superantigens (SPE-G, SPE-H, SPE-J and SMEZ-2) and the corresponding polynucleotides which encode them.

FIG. 1 shows the amino acid sequence of the above four superantigens together with those of previously identified superantigen SMEZ (SEQ ID NO:9), SPE-C (SEQ ID NO:10), and SEA (SEQ ID NO:11).

Of the four superantigens SPE-G, SPE-H, SPE-J and SMEZ-2, the latter is perhaps of greatest interest.

The smez-2 gene which encodes SMEZ-2 was identified in an experiment designed to produce recombinant SMEZ protein from *S. pyogenes* 2035 genomic DNA. A full length smez gene was isolated from the strain but the DNA sequence of the smez gene of strain 2035 showed nucleotide changes in 36 positions (or 5%) compared to smez from strain M1 (FIG. 1). The deduced protein sequences differed in 17 amino acid residues (or 8.1%). This difference establishes this as a new gene, smez-2, and the encoded protein as a new superantigen, SMEZ-2.

The most significant difference between SMEZ and SMEZ-2 is an exchanged pentapeptide sequence at position 96-100, where the EEPMS (SEQ ID NO:23) sequence of SMEZ is converted to KTSIP (SEQ ID NO:25) in SMEZ-2 (FIG. 2). A second difference is at position 111-112, where an RR dipeptide is exchanged for GK in SMEZ-2. The remaining 10 different residues are spread over almost the entire primary sequence.

FIG. 2 (SEQ ID NOS:1-2) shows the nucleotide sequence encoding mature SMEZ-2 and the deduced amino acid sequence.

Likewise, FIGS. 3 to 5 (SEQ ID NOS:3-8) show the nucleotide sequence encoding mature SPE-G, SPE-H, SPE-J superantigens, respectively, together with their respective deduced amino acid sequences.

The invention is of course not restricted to superantigens/polynucleotides having the specific sequences of FIGS. 1 (SEQ ID NOs:9, 20, 8, 10, 21, 22, and 11, respectively) to 5 (SEQ ID NOs:1-8). Instead, functionally equivalent variants are contemplated.

The phrase "functionally equivalent variants" recognises that it is possible to vary the amino acid/nucleotide sequence of a peptide while retaining substantially equivalent functionality. For example, a peptide can be considered a functional equivalent of another peptide for a specific function if the equivalent peptide is immunologically cross-reactive with and has at least substantially the same function as the original peptide. The equivalent can be, for example, a fragment of the peptide, a fusion of the peptide with another peptide or carrier, or a fusion of a fragment which additional amino acids. For example, it is possible to substitute amino acids in a sequence with equivalent amino acids using conventional techniques. Groups of amino acids normally held to be equivalent are:

(a) Ala, Ser, Thr, Pro, Gly;

(b) Asn, Asp, Glu, Gln;

(c) His, Arg, Lys;

(d) Met, Leu, Ile, Val; and (e) Phe, Tyr, Trp.

Equally, nucleotide sequences encoding a particular product can vary significantly simply due to the degeneracy of the nucleic acid code.

Variants can have a greater or lesser degree of homology as between the variant amino acid/nucleotide sequence and the original.

Polynucleotide or polypeptide sequence may be aligned, and percentage of identical nucleotides in a specified region may be determined against another sequence, using computer algorithms that are publicly available. Two exemplary algorithms for aligning and identifying the similarity of polynucleotide sequence are the BLASTN and FASTA algorithms. The similarity of polypeptide sequences may be examined using the BLASTP algorithm. Both the BLASTN and BLASTP software are available on the NCBI anonymous FTP server (ncbi.nlm.nih.gov) under /blast/executables/. The BLASTN algorithm version 2.0.4 [Feb. 24, 1998], set to the default parameters described in the documentation of variants according to the present invention. The use of the BLAST family of algorithms, including BLASTN and BLASTP, is described at NCBI's website at URL ncbi.nlm.nih.gov/BLAST/newblast.html and in the publication of Altschul, Stephen F., et al. (1997), "Gapped BLAST and PSI-BLAST: a new generation of protein database search programs", *Nucleic Acids Res.* 25:3389-3402. The computer algorithm FASTA is available on the Internet at the ftp site ftp.virginia.edu/pub/fasta/. Version 2.0u4, February 1996, set to the default parameters described in the documentation and distributed with the algorithm, is also preferred for use in the determination of variants according to the present invention. The use of the FASTA algorithm is described in W. R. Pearson and D. J. Lipman, "Improved Tools for Biological Sequence Analysis", *Proc. Natl. Acad. Sci. USA* 85:2444-2448 (1988)

and W. R. Pearson, "Rapid and Sensitive Sequence Comparison with FASTP and FASTA, "*Methods in Enzymology* 183: 63-98 (1990).

The following running parameters are preferred for determination of alignments and similarities using BLASTN that contribute to E values (as discussed below) and percentage identity: Unix running command: blastall -p blastn -d embldb -e 10-G 1 -E 1 -r 2 -v 50 -b 50 -I queryseq -o results; and parameter default values:

-p Program Name [String]
-d Database [String]
-e Expectation value (E) [Real]
-G Cost to open a gap (zero invokes default behaviour) [Integer]
-E Cost to extend a cap (zero invokes default behaviour) [Integer]
-r Reward for a nucleotide match (blastn only) [Integer]
-v Number of one-line descriptions (V) [Integer]
-b Number of alignments to show (B) [Integer]
-i Query File [File In]
-o BLAST report Output File [File Out] Optional For BLASTP the following running parameters are preferred: blastall -p blastp -d swissprotdb -e 10 -G 1 -E 1 -v 50 -b 50 -I queryseq -o results -p Program Name [String]
-d Database [String]
-e Expectation value (E) [Real]
-G Cost to open a gap (zero invokes default behaviour) [Integer]
-E Cost to extend a cap (zero invokes default behaviour) [Integer]
-v Number of one-line descriptions (v) [Integer]
-b Number of alignments to show (b) [Integer]
-i Query File [File In]
-o BLAST report Output File [File Out] Optional The "hits" to one or more database sequences by a queried sequence produced by BLASTN, BLASTP, FASTA, or a similar algorithm, align and identify similar portions of sequences. The hits are arranged in order of the degree of similarity and the length of sequence overlap. Hits to a database sequence generally represent an overlap over only a fraction of the sequence length of the queried sequence.

The BLASTN and FASTA algorithms also produce "Expect" or E values for alignments. The E value indicates the number of hits one can "expect" to see over a certain number of contiguous sequences by chance when searching a database of a certain size. The Expect value is used as a significance threshold for determining whether the hit to a database, such as the preferred EMBL database, indicates true similarity. For example, an E value of 0.1 assigned to a hit is interpreted as meaning that in a database of the size of the EMBL database, one might expect to see 0.1 matches over the aligned portion of the sequence with a similar score simply by chance. By this criterion, the aligned and matched portions of the sequences then have a 90% probability of being the same. For sequences having an E value of 0.01 or less over aligned and matched portions, the probability of finding a match by chance in the EMBL database is 1% or less using the BLASTN or FASTA algorithm.

According to one embodiment, "variant" polynucleotides, with reference to each of the polynucleotides of the present invention, preferably comprise sequences having the same number or fewer nucleic acids than each of the polynucleotides of the present invention and producing an E value of 0.01 or less when compared to the polynucleotide of the present invention. That is, a variant polynucleotide is any sequence that has at least a 99% probability of being the same as the polynucleotide of the present invention, measured as having an E value of 0.01 or less using the BLASTN or FASTA algorithms set at the parameters discussed above.

Variant polynucleotide sequences will generally hybridize to the recited polynucleotide sequence under stringent conditions. As used herein, "stringent conditions" refers to prewashing in a solution of 6×SSC, 0.2% SDS; hybridizing at 65° C., 6×SSC, 0.2% SDS overnight; followed by two washes of 30 minutes each in 1×SSC, 0.1% SDS at 65° C. and two washes of 30 minutes each in 0.2×SSC, 0.1% SDS at 65° C.

The superantigens of the invention together with their fragments and other variants may be generated by synthetic or recombinant means. Synthetic polypeptides having fewer than about 100 amino acids, and generally fewer than about 50 amino acids, may be generated by techniques well known to those of ordinary skill in the art. For example, such peptides may be synthesised using any of the commercially available solid-phase techniques such as the Merryfield solid phase synthesis method, where amino acids are sequentially added to a growing amino acid chain (see Merryfield, J. Am. Chem. Soc 85: 2146-2149 (1963)). Equipment for automative synthesis of peptides is commercially available from suppliers such as Perkin Elmer/Applied Biosystems, Inc. and may be operated according to the manufacturers instructions.

Each superantigen, or a fragment or variant thereof, may also be produced recombinantly by inserting a polynucleotide (usually DNA) sequence that encodes the superantigen into an expression vector and expressing the superantigen in an appropriate host. Any of a variety of expression vectors known to those of ordinary skill in the art may be employed. Expression may be achieved in any appropriate host cell that has been transformed or transfected with an expression vector containing a DNA molecule which encodes the recombinant protein. Suitable host cells includes procaryotes, yeasts and higher eukaryotic cells. Preferably, the host cells employed are *E. coli*, yeasts or a mammalian cell line such as COS or CHO, or an insect cell line, such as SF9, using a baculovirus expression vector. The DNA sequence expressed in this matter may encode the naturally occurring superantigen, fragments of the naturally occurring protein or variants thereof.

DNA sequences encoding the superantigen or fragments may be obtained, for example, by screening an appropriate *S. pyogenes* cDNA or genomic DNA library for DNA sequences that hybridise to degenerate oligonucleotides derived from partial amino acid sequences of the superantigen. Suitable degenerate oligonucleotides may be designed and synthesised by standard techniques and the screen may be performed as described, for example, in Maniatis et al. Molecular Cloning—A Laboratory Manual, Cold Spring Harbour Laboratories, Cold Spring Harbour, N.Y. (1989).

Identification of these superantigens and of their properties gives rise to a number of useful applications. A first such application is in the genotyping of organisms by reference to their superantigen profile.

An illustration of this is subtyping of strains of *S. pyogenes*.

One feature which has been observed is that all clones of *S. pyogenes* so far found to be positive for SMEZ express either SMEZ-1 or SMEZ-2 but not both. Thus they are mutually exclusive, which enables a rapid diagnostic test which tells whether an isolate or a patient sample is either SMEZ-1+ve or SMEZ-2+ve. This will assist in the typing of the isolate.

This general diagnostic approach is most simply achieved by providing a set of primers which amplify either all or a subset of superantigen genes and that generate gene specific fragments. This can be modified to provide a simple qualitative ELISA-strip type kit that detects biotin labelled PCR fragments amplified by the specific primers and hybridised to immobilised sequence specific probes. This has usefulness for screening patient tissue samples for the presence of superantigen producing streptococcal strains.

Such approaches are well known and well understood by those persons skilled in the art.

Another approach is to provide monoclonal antibodies to detect each of the streptococcal superantigens. An ELISA kit containing such antibodies would allow the screening of large numbers of streptococcal isolates. A kit such as this would be useful for agencies testing for patterns in streptococcal disease or food poisoning outbreaks.

Another potential diagnostic application of the superantigens of the invention is in the diagnosis of disease, such as Kawasaki Syndrome (KS).

KS is an acute multi-system vasculitis of unknown aetiology. It occurs world-wide but is most prevalent in Japan or in Japanese ancestry. It primarily affects infants and the young up to the age of 16. It is an acute disease that without treatment, can be fatal. Primary clinical manifestations include Prolonged fever
Bilateral non-exudative conjunctivitis
Indurtation and erythema of the extremities
Inflammation of the lips and oropharynx
Polymorphous skin rash
Cervical lymphoadenopathy
In 15-25% of cases, coronary arterial lesions develop.

These indications are used as a primary diagnosis of KS.

In Japan and the US, KS has become one of the most common causes of acquired heart disease in children. Treatment involves the immediate intravenous administration of gamma globulin (IVGG) during the acute phase of the disease and this significantly reduces the level of coronary lesions.

There are two clear phases to the disease, an acute phase and a convalescent phase. The acute phase is marked by strong immune activation. Several reports have suggested that superantigens are involved and many attempts have been made to link the disease to infection with superantigen producing strains of *Streptococcus pyogenes*. Features of the acute phase of KS are the expansion of Vβ2 and to a lesser extent Vβ8 bearing T cells and an increase of DR expression T cells (a hallmark of T cell activation).

Because SMEZ-2 stimulates both Vβ2 and Vβ8 bearing T cells, testing for SMEZ-2 production is potentially very useful in the diagnosis of KS.

Antibodies to the superantigens for use in applications such as are described above are also provided by this invention. Such antibodies can be polyclonal but will preferably be monoclonal antibodies.

Monoclonal antibodies with affinities of $10^{-8}$ $M^{-1}$ or preferably $10^{-9}$ to $10^{-10}$ $M^{-1}$ or stronger will typically be made by standard procedures as described, eg. in Harlow & Lane (1988) or Goding (1986). Briefly, appropriate animals will be selected and the desired immunization protocol followed. After the appropriate period of time, the spleens of such animals are excised and individual spleen cells fused, typically, to immortalised myeloma cells under appropriate selection conditions. Thereafter, the cells are clonally separated and the supernatants of each clone tested for their production of an appropriate antibody specific for the desired region of the antigen.

Other suitable techniques for preparing antibodies well known in the art involve in vitro exposure of lymphocytes to the antigenic polypeptides, or alternatively, to selection of libraries of antibodies in phage or similar vectors.

Also, recombinant immunoglobulins may be produced using procedures known in the art (see, for example, U.S. Pat. No. 4,816,567 and Hodgson J. (1991)).

The antibodies may be used with or without modification. Frequently, antibodies will be labeled by joining, either covalently or non-covalently, a substance which provides for a detectable signal. A wide variety of labels and conjugation techniques are known and are reported extensively in the literature. Suitable labels include radionuclides, enzymes, substrates, cofactors, inhibitors, fluorescent agents, chemiluminescent agents, magnetic particles and the like. Patents teaching the use of such labels include U.S. Pat. Nos. 3,817,837; 3,850,752; 3,939,350; 3,996,345; 4,277,437; 4,275,149; and 4,366,241.

The immunological assay in which the antibodies are employed can involve any convenient format known in the art.

The nucleotide sequence information provided herein may be used to design probes and primers for probing or amplification of parts of the smez-2, spe-g, spe-h and spe-j genes. An oligonucleotide for use in probing or PCR may be about 30 or fewer nucleotides in length. Generally, specific primers are upwards of 14 nucleotides in length. For optimum specificity and cost effectiveness, primers or 16-24 nucleotides in length are preferred. Those skilled in the art are well versed in the design of primers for use in processes such as PCR.

If required, probing can be done with entire polynucleotide sequences provided herein as SEQ ID NOS 1, 3, 5 and 7, optionally carrying revealing labels or reporter molecules.

Such probes and primers also form aspects of the present invention.

Probing may employ the standard Southern blotting technique. For instance, DNA may be extracted from cells and digested with different restriction enzymes. Restriction fragments may then be separated by electrophoresis on an agarose gel, before denaturation and transfer to a nitrocellulose filter. Labelled probes may be hybridised to the DNA fragments on the filter and binding determined. DNA for probing may be prepared from RNA preparations from cells. Probing may optionally be done by means of so-called "nucleic acid chips" (see Marshall and Hodgson (1998) *Nature Biotechnology* 16:27-31).

In addition to diagnostic applications, another application of the superantigens is reliant upon their ability to bind to other cells.

One of the most important features of superantigens is that they bind a large number or T cell receptor molecules by binding to the Vβ domain. They are the most potent of all T cell mitogens and are therefore useful to recruit and activate T cells in a relatively non-specific fashion.

This ability enables the formation of constructs in which the superantigen (or at least the T-cell binding portion of it) is coupled to a cell-targeting molecule, particularly an antibody, more usually a monoclonal antibody.

When a monoclonal antibody that targets a specific cell surface antigen (such as a tumor specific antigen) is coupled to a superantigen in such a construct, this generates a reagent that on the one hand will bind specifically to the tumor cell, and on the other hand recruit and selectively active T cells for the purpose of killing the targeted cell.

Bi-specific constructs of this type have important applications in therapy (particularly cancer therapy) and again may be prepared by means known to those skilled in art. For example SMEZ-2 may be coupled to a tumor specific monoclonal antibody. The constructs may be incorporated into conventional carriers for pharmaceutically-active proteins.

Various aspects of the invention will now be described with reference to the following experimental section, which is included for illustrative purposes.

EXAMPLE

Section A: Superantigen Identification and Characterisation

Materials and Methods

Identification of Novel SAGs

The novel superantigens were identified by searching the *S. pyogenes* M1 genome database at the University of Oklahoma (genome.ou.edu/strep.html) with highly conserved β5 and α4 regions of streptococcal and staphylococcal superantigens, using a TBlastN search programme.

The open reading frames were defined by translating the DNA sequences around the matching regions and aligning the protein sequences to known superantigens using the computer programmes Gap. Multiple alignments and dendrograms were performed with Lineup and Pileup. The FASTA programme was used for searching the SwissProt (Amos Bairoch, Switzerland) and PIR (Protein Identification Resource, USA) protein databases.

The leader sequences of SPE-G and SPE-H were predicted using the SP Scan programme All computer programmes are part of the GCG package (version 8).

Cloning of smez, smez-2, spe-g and spe-h.

Fifty nanograms of *S. pyogenes* M1 (ATCC 700294) or *S. pyogenes* 2035 genomic DNA was used as a template to amplify the smez DNA fragment and the smez-2 DNA fragment, respectively, by PCR using the primers smez-forward (TGGGATCCTTAGAAGTAGATAATA) (SEQ ID NO:12) and smez-reverse (AAGAATTCTTAGGAGTCAATTTC) (SEQ ID NO:13) and Taq Polymerase (Promega). The primers contain a terminal tag with the resfriction enzyme recognition sequences BamHI and EcoRI, respectively. The amplified DNA fragment, encoding the mature protein without the leader sequence (Kamazawa et al, 1997 Infect. Immun. 65 no. 9:38281-33) was cloned into a T-tailed pBlueScript SKII vector (Stratagene).

Spe-g and spe-h were cloned in similar approach, using the primers spe-g-fw

```
primers
spe-g-fw      (CTGGATCCGATGAAAATTTAAAAGATTTAA)
and spe-g-rev     (AAGAATTCGGGGGGAGAATAG),
and primers
spe-h-fw      (TTGGATCCAATTCTTATAATACAACC)
and spe-h-rev     (AAAAGCTTTTAGCTGATTGACAC),
respectively.
```

The DNA sequences of the subcloned toxin genes were confirmed by the dideoxy chain termination method using a Licor automated DNA sequencer. As the DNA sequences from the genomic database are all unedited raw data, 3 subclones of every cloning experiment were analyzed to ensure that no Taq polymerase related mutations were introduced.

Expression and Purification of rSMEZ, rSMEZ-2, rSPE-G and rSPE-H.

Subcloned smez, smez-2 and spe-g fragments were cut from pBlueScript SKII vectors, using restriction enzymes BamHI and EcoRI (LifeTech), and cloned into pGEX-2T expression vectors (Pharmacia). Due to an internal EcoRI restriction site within the spe-H gene, the pBlueScript:spe-h subclone was digested with BamHI and HindIII and the spe-h fragment was cloned into a modified pGEX-2T vector that contains a HindIII 3' cloning site.

Recombinant SMEZ, rSMEZ-2 and rSPE-H were expressed in *E. coli* DH5α cells as glutathione-S-tranferase (GST) fusion proteins. Cultures were grown at 37° C. and induced for 3-4 h after adding 0.2 mM isopropyl-β-D-thiogalactopyranoside (IPTG). GST—SPE-G fusion protein was expressed in cells grown at 28° C.

The GST fusion proteins were purified on glutathione agarose as described previously (Li et al, 1997) and the mature toxins were cleaved off from GST by trypsin digestion. All recombinant toxins, except rSMEZ, were further purified by two rounds of cation exchange chromatography using carboxy methyl sepharose (Pharmacia). The GST-SMEZ fusion protein was trypsin digested on the GSH-column and the flow through containing the SMEZ was collected.

Gel Electrophoresis

All purified recombinant toxins were tested on a 12% SDS-polyacrylamide gel according the procedure of Laemmli. The isoelectric point of the recombinant toxins was determined by isoelectric focusing on a 5.5% polyacrylamide gel using ampholine pH 5-8 (Pharmacia Biotech). The gel was run for 90 min at 1 W constant power.

Toxin Proliferation Assay

Human peripheral blood lymphocytes (PBL) were purified from blood of a healthy donor by Histopaque Ficoll (Sigma) fractionation. The PBL were incubated in 96-well round bottom microtiter plates at $10^5$ cells per well with RPMI-10 (RPMI with 10% fetal calf serum) containing varying dilutions of recombinant toxins. The dilution series was performed in 1:5 steps from a starting concentration of 10 ng/ml of toxin. Pipette tips were changed after each dilution step. After 3 days 0.1 μCi [$^3$H]thymidine was added to each well and cells were incubated for another 24 h. Cells were harvested and counted on a scintillation counter.

Mouse leukocytes were obtained from spleens of 5 different mouse strains (SJL, B10.M, B10/J, C3H and BALB/C). Splenocytes were washed in DMEM-10, counted in 5% acetic acid and incubated on microtiter plates at $10^5$ cells per well with DMEM-10 and toxins as described for human PBLs.

TcR Vβ analysis.

Vβ enrichment analysis was performed by anchored multiprimer amplification (Hudson et al, 1993, J exp Med 177: 175-185). Human PBLs were incubated with 20 pg/ml of recombinant toxin at $10^6$ cells/ml for 3 d. A two-fold volume expansion of the culture followed with medium containing 20 ng/ml IL-2. After another 24 h, stimulated and resting cells were harvested and RNA was prepared using Trizol reagent (Life Tech). A 500 bp β-chain DNA probe was obtained by anchored multiprimer PCR as described previously (38), radiolabeled and hybridized to del (36) individual Vβs and a Cβ DNA region dot blotted on a Nylon membrane. The membrane was analysed on a Molecular Dynamics Storm Phosphor imager using ImageQuant software. Individual Vβs were expressed as a percentage of all the Vβs determined by hybridization to the Cβ probe.

Jurkat Cell Assay

Jurkat cells (a human T cell line) and LG-2 cells (a human B lymphoblastoid cell line, homozygous for HLA-DR1) were harvested in log phase and resuspended in RPMI-10. One hundred microliter of the cell suspension, containing $1 \times 10^5$ Jurkat cells and $2 \times 10^4$ LG-2 cells were mixed with 100 μl of varying dilutions of recombinant toxins on 96 well plates. After incubating overnight at 37° C., 100 μl aliquots were transfered onto a fresh plate and 100 μl ($1 \times 10^4$) of SeI cells (IL-2 dependent murine T cell line) per well were added. After incubating for 24 h, 0.1 µCi [³H]thymidine was added to each well and cells were incubated for another 24 h. Cells were harvested and counted on a scintillation counter. As a control, a dilution series of IL-2 was incubated with SeI cells.

Computer Aided Modelling of Protein Structures

Protein structures of SMEZ-2, SPE-G and SPE-H were created on a Silicon Graphics computer using InsightII/Homology software. The superantigens SEA, SEB and SPE-C were used as reference proteins to determine structurally conserved regions (SCRs). Coordinate files for SEA (1ESF), for SEB (1SEB) and for SPE-C (1AN8) were downloaded from the Brookhaven Protein Database. The primary amino acid sequences of the reference proteins and SMEZ-2, SPE-G and SPE-H, respectively, were aligned and coordinates from superimposed SCR's were assigned to the model proteins. The loop regions between the SCRs were generated by random choice. MolScript software (P J Kraulis, 1991, J App Critallography 24:946-50) was used for displaying the computer generated images.

Radiolabeling and LG2 Binding Experiments

Recombinant toxin was radioiodinated by the chloramine T method as previously described (by Li et al. 1997). Labeled toxin was seperated from free iodine by size exclusion chromatography using Sephadex G25 (Pharmacia). LG2 cells were used for cell binding experiments, as described (Li et al. 1997). Briefly, cells were harvested, resuspended in RPMI-10 and mixed at $10^6$ cells/ml with $^{125}$I-tracer toxin (1 ng) and 0.0001 to 10 µg of unlabeled toxin and incubated at 37° C. for 1 h. After washing with ice cold RPMI-1 the pelleted cells were analyzed in a gamma counter. For zinc binding assays the toxins were incubated in either RPMI-10 alone, in RPMI-10 with 1 mM EDTA or in RPMI-10 with 1 mM EDTA, 2 mM $ZnCl_2$.

Scatchard analysis was performed as described by Cunningham et al. (1989). For competitive binding studies, 1 ng of $^{125}$I-tracer toxin (rSMEZ, rSMES-2, rSPE-G, rSPE-H, rSEA, rSPE-C, or rTSST) was incubated with 0.0001 to 10 µg of unlabeled toxin (rSMEZ, rSMES-2, rSPE-G, rSPE-H, rSEA, rSEB, rSPE-C, and rTSST) for 1 h. For SEB inhibition studies, 20 ng of $^{125}$I-rSEB was used as tracer and samples were incubated for 4 h.

Results

Identification and Sequence Analysis of Superantigens.

The Oklahoma University *Streptococcus pyogenes* M1 genome database is accessible via the internet and contains a collection of more than 300 DNA sequence contigs derived from a shot gun plasmid library of the complete *S. pyogenes* M1 genome. The currently available DNA sequences cover about 95% of the total genome. This database was searched with a highly conserved superantigen peptide sequence, using a search program that screens the DNA database for peptide sequences in all 6 possible reading frames. 8 significant matches and predicted the open reading frames (ORFs) were found by aligning translated DNA sequences to complete protein sequences of known SAgs.

Five matches gave complete ORFs with significant homology to streptococcal and staphylococcal superantigens. Three of these ORFs correlate to SPE-C, SSA and the recently described SMEZ (Kamezawa et al. 1997), respectively. The remaining two ORFs could not be correlated to any known protein in the SwissProt and PIR databases. These novel putative superantigen genes were named spe-g and spe-h (see FIGS. 3 and 4). One ORF could not be generated completely due to its location close to the end of a contig. The DNA sequence of the missing 5'-end is located on another contig, and individual contigs have yet to be assembled in the database. However, the available sequence shows an ORF for the 137 COOH-terminal amino acid residues of a putative novel superantigen which could not be found in the existing protein databases. This gene was named spe-j (see FIG. 5).

In two cases a complete ORF could not be defined due to several out-of-frame mutations. Although DNA sequencing errors on the unedited DNA sequences cannot be completely ruled out, the high frequency of inserts and deletions probably represent natural mutation events on pseudogenes, which are no longer used.

To produce recombinant proteins of SMEZ, SPE-G and SPE-H, individual genes (coding for the mature toxins without leader sequence) were amplified by PCR, and subcloned for DNA sequencing. Both, *Str. pyogenes* M1 and *Str. pyogenes* 2035 genomic DNA were used and individual toxin gene sequences compared between the two strains. The spe-h gene was isolated from M1 strain, but could not be amplified from strain 2035 genomic DNA suggesting a restricted strain specificity for this toxin. The spe-g gene was cloned from both M1 and 2035, and DNA sequence analysis of both genes showed no differences. The full length smez gene was isolated from both strains, but DNA sequence comparison revealed some striking differences. The smez gene of strain 2035 showed nucleotide changes in 36 positions (or 5%) compared to smez from strain M1 (FIG. 1). The deduced protein sequences differed in 17 amino acid residues (or 8.1%). This difference was sufficient to indicate a new gene. This gene was named smez-2, because it is 95% homologous to smez (see FIG. 2).

The most significant different between SMEZ and SMEZ-2 is an exchanged pentapeptide sequence at position 96-100, where the EEPMS (SEQ ID NO:23) sequence of SMEZ is converted to KTSIP (SEQ ID NO:25) in SMEZ-2 (FIG. 2). A second difference is at position 111-112, where an RR dipeptide is exchanged for GK in SMEZ-2. The remaining 10 different residues are spread over almost the entire primary sequence.

A revised superantigen family tree, based on primary amino acid sequence homology now shows 3 general subfamilies; group A comprises SPE-C, SPE-J, SPE-G, SMEZ and SMEZ-2, group B comprises SEC1-3, SEB, SSA, SPE-A and SEG and group C comprises SEA, SEE, SED, SEH and SEI. Two superantigens, TSST and SPE-H do not belong to any one of those subfamilies.

SMEZ, SMEZ-2, SPE-G and SPE-J are most closely related to SPE-C, increasing the number of this subfamily from 2 to 5 members. SPE-G shows the highest protein sequence homology with SPE-C (38.4% identity and 46.6% similarity). The homology of SPE-J to SPE-C is even more significant (56% identity and 62% similarity), but this comparison is only preliminary due to the missing $NH_2$-terminal sequence. SMEZ shows 30.9%/40.7% homology to SPE-C and SMEZ-2 is 92%/93% homologous to SMEZ.

SPE-H builds a new branch in the family tree and is most closely related to SED, showing 25% identity and 37.3% similarity.

Multiple alignment of Sag protein sequences (FIG. 1) SEQ ID NOs:9, 20, 8, 10, 21, 22 and 11, respectively, in order of appearance) shows that similarities are clustered within structure determining regions, represented by α4, α5, β4, and β5 regions. This applies to all toxins of the superantigen family (data not shown) and explains why superantigens like SPE-C and SEA have very similar overall structures despite their rather low sequence identity of 24.4%.

Although SPE-H is less related to SPE-C it shows 2 common features with the "SPE-C subfamily": (I) a truncated $NH_2$-terminus, lacking the α1 region and (II) a primary zinc binding motif (H-X-D) at the C-terminus (FIG. 1). It has been shown for several superantigens that this motif is involved in a zinc coordinated binding to the β-chain of HLA-DR1.

Fusion proteins of GST-SMEZ, GST-SMEZ-2 and GST-SPE-H were completely soluble and gave yields of about 30 mg per liter. The GST-SPE-G fusion was insoluble when grown at 37° C., but mostly soluble when expressed in cells growing at 28° C. Although soluble GST-SPE-G yields were 20-30 mg per liter, solubility decreased after cleavage of the fusion protein with trypsin. Soluble rSPE-G was achieved by diluting the GST-SPE-G to less than 0.2 mg/ml prior to cleavage. After cation exchange chromatography, purified rSPE-G could be stored at about 0.4 mg/ml.

Recombinant SMEZ could not be separated from GST by ion exchange chromatography. Isoelectric focusing revealed that the isoelectric points of the two proteins are too similar to allow separation (data not shown). Therefore, rSMEZ was released from GST by cleaving with trypsin while still bound to the GSH agarose column. Recombinant SMEZ was collected with the flow through.

The purified recombinant toxins were applied to SDS-PAGE and isoelectric focusing (FIG. 6). Each toxin ran as a single band on the SDS PAA gel confirming their purity and their calculated molecular weights of 24.33 (SMEZ), 24.15 (SMEZ-2), 24.63 (SPE-G) and 23.63 (SPE-H) (FIG. 6A). The isoelectric focusing gel (FIG. 6B shows a significant difference between rSMEZ and rSMEZ-2. Like most other staphylococcal and streptococcal toxins, rSMEZ-2 possesses a slightly basic isoelectric point at pH 7-8, but rSMEZ is acidic with an IEP at pH 6-6.5.

T Cell Proliferation and Vβ Specificity

To ensure the native conformation of the purified recombinant toxins, a standard [$^3$H]thymidine incorporation assay was performed to test for their potency to stimulate peripheral blood lymphocytes (PBLs). All toxins were active on human T cells (FIG. 7). Recombinant SEA, rSEB, rSPE-C and RTSST were included as reference proteins. The mitogenic potency of these toxins was lower than described previously, but is regarded as a more accurate figure. In previous studies, a higher starting concentration of toxin (100 ng/ml) was used and tips were not changed in between dilutions. This led to significant carryover across the whole dilution range. On this occasion, the starting concentration was 10 ng/ml and tips were changed in between dilutions preventing any carryover.

The half maximal response for rSPE-G and rSPE-H was 2 pg/ml and 50 pg/ml, respectively. No activity was detected at less than 0.02 pg/ml and 0.1 pg/ml, respectively. Both toxins are therefore less potent than rSPE-C. Recombinant SMEZ was similar in potency to rSPE-C, with a $P_{50\%}$ value of 0.08 pg/ml and no detectable proliferation at less than 0.5 fg/ml. Recombinant SMEZ-2 showed the strongest mitogenic potency of all toxins tested or, as far as can be determined, described elsewhere. The $P_{50\%}$ value of 0.02 pg/ml and rSMEZ-2 was still active at less than 0.1 fg/ml. All $P_{50\%}$ values are summarized in Table 1.

TABLE 1

POTENCY OF RECOMBINANT TOXINS ON HUMAN AND MOUSE T CELLS.
PROLIFERATION POTENTIAL $P_{50\%}$ [pg/ml]

| TOXIN | HUMAN | SJL | B10.M | B10/J | C3H | BALB/C |
|---|---|---|---|---|---|---|
| SEA | 0.1 | 20 | 12 | 1.8 | 19 | 1000 |
| SEE | 0.2 | 10 | 12 | 1.5 | 50 | 15 |
| SEB | 0.8 | 7000 | 80,000 | 5000 | 10,000 | 1000 |
| TSST | 0.2 | 20 | 1000 | 1.2 | 100 | 10 |
| SPE-C | 0.1 | >100,000 | >100,000 | >100,000 | >100,000 | >100,000 |
| SMEZ | 0.08 | 80 | 80 | 100 | 9000 | 200 |
| SMEZ-2 | 0.02 | 100 | 15 | 10 | 800 | 18 |
| SPE-G | 2 | >100,000 | >100,000 | >100,000 | >100,000 | >100,000 |
| SPE-H | 50 | 15 | 800 | 5000 | 100 | 1000 |

Human PBLs and mouse T cells were stimulated with varying amounts of recombinant toxin. The $P_{50\%}$ value reflects the concentration of recombinant toxin required to induce 50% maximal cell proliferation. No proliferation was detected for rSPE-C and rSPE-G at any concentration tested on murine T cells.

Murine T cells from 5 different mouse strains were tested for their mitogenic response to rSMEZ, rSMEZ-2, rSPE-G and rSPE-H (Table 1). Recombinant SPE-G showed no activity against any of the mouse strains tested. Recombinant SPE-H, rSMEZ and rSMEZ-2 showed varied potency depending on the individual mouse strain. For example, rSMEZ-2 was 500-fold more potent than rSPE-H in the B10/J strain, while rSPE-H was 7.5-fold more active than rSMEZ-2 in the SJL strain.

The most consistently potent toxin on murine T cells was rSMEZ-2 with Pso % values of 10 pg/ml in B10/J and 800 pg/ml in C3H. Recombinant SMEZ varied between 80 pg/ml in SJL and B10.M and 9000 pg/ml in C3H. The $P_{50\%}$ value for rSPE-H was between 15 pg/ml in SJL and 5000 pg/ml in B10/J.

TABLE 2

Vβ SPECIFICITY OF RECOMBINANT TOXINS ON HUMAN PBLS.
PERCENT Vβ ENRICHMENT

| Vβ | Resting | SMEZ | SMEZ-2 | SPE-G | SPE-H |
|---|---|---|---|---|---|
| 1.1 | 0.2 | 0.3 | 0.4 | 1.2 | 1 |
| 2.1 | 0.4 | <u>8.4</u> | 1 | <u>17.9</u> | <u>8.6</u> |
| 3.2 | 4.8 | 3.1 | 2.5 | 3 | 2.4 |
| 4.1 | 3.5 | <u>24.8</u> | <u>14.4</u> | <u>11.2</u> | 5.2 |
| 5.1 | 6.2 | 1.4 | 2.5 | 5.7 | 2.2 |
| 5.3 | 5.6 | 2.2 | 4.1 | 4.7 | 4.1 |
| 6.3 | 3 | 0.8 | 2.3 | 4.7 | 3.5 |
| 6.4 | 5.4 | 2.1 | 5.9 | 9.6 | 5.6 |
| 6.9 | 6.9 | 3.5 | 9.3 | <u>19.1</u> | 12.2 |
| 7.3 | 3.5 | <u>15.3</u> | 7.3 | 3.2 | <u>12.6</u> |
| 7.4 | 9 | 13.5 | 11.7 | 2.9 | 6.3 |
| 8.1 | 8.7 | <u>20.7</u> | <u>36</u> | 4.5 | 2.4 |
| 9.1 | 0.3 | 0.05 | 0 | <u>1.2</u> | <u>2.3</u> |

TABLE 2-continued

Vβ SPECIFICITY OF RECOMBINANT TOXINS ON
HUMAN PBLS.
PERCENT Vβ ENRICHMENT

| Vβ | Resting | SMEZ | SMEZ-2 | SPE-G | SPE-H |
|---|---|---|---|---|---|
| 12.3 | 0.8 | 1.6 | 2 | <u>3.2</u> | 2.6 |
| 12.5 | 3 | 1.2 | 2 | 3 | 2.3 |
| 15.1 | 0.6 | 0.5 | 0.7 | 1.2 | 0.8 |
| 23.1 | 0.2 | 0.1 | 0.3 | 0.8 | <u>1</u> |
| total | 62.1 | 99.7 | 102.8 | 97.1 | 75.2 |

Human PBLs were incubated with 20 pg/ml of recombinant toxin for 4d.
Relative enrichment of Vβ cDNAs was analyzed from RNA of stimulated and reting PBLs by anchored primer PCR and reverse dot blot to a panel of 17 different Vβ cDNAs.
The values representing the highest Vβ enrichment are underlined.

The human TcR Vβ specificity of the recombinant toxins was determined by multiprimer anchored PCR and dot blot analysis using a of 17 human Vβ DNA regions. The Vβ enrichment after stimulation with toxin was compared to the Vβ profile of unstimulated PBLs (Table 2). The sum total of all Vβs stimulated by rSMEZ, rSMEZ-2 and rSPE-G was close to 100% suggesting that the Vβs used in the panel represent all the targeted Vβs. On the other hand, the total of the Vβs stimulated by rSPE-H was only 75%. It is therefore likely that rSPE-H also stimulated some less common Vβs, which are not represented in the panel. The most dramatic response was seen with all toxins, except rSMEZ2, on Vp2.1 bearing T cells (21-fold for rSMEZ, 45-fold for rSPE-G and 22-fold for rSPE-H). In contrast, rSMEZ2 gave only a 2.5-fold increase of Vβ2.1 T-cells. SPE-G also targeted Vβ4.1, Vβ6.9, Vβ9.1 and Vβ12.3 (3-4 fold). A moderate enrichment of Vβ12.6, Vβ9.1 and Vβ23.1 (4-8 fold) was observed with rSPE-H. Both, rSMEZ and rSMEZ2, targeted Vβ4.1 and Vβ8.1 with similiar efficiency (3-7-fold). This finding is of particular interest, because Vβ8.1 activity had been found in some, but not all Str. pyogenes culture supernatants and in crude preparations of SPE-A and SPE-C. Moreover, SPE-B has often been claimed to have Vβ8 specific activity, but has since been shown to be a contaminant previously called SpeX. The ability of rSMEZ and rSMEZ-2 to stimulate the Vβ8.1 Jurkat cell line was tested (FIG. 8) Recombinant SMEZ was less potent than the control toxin (rSEE), showing a half maximal response of 0.2 ng/ml, compared to 0.08 ng/ml with rSEE, but rSMEZ-2 was more potent than rSEE (0.02 ng/ml). No proliferation activity was observed with the negative control toxin rSEA.

MHC Class II Binding

To determine if there were significant structural differences, the protein structures of SMEZ-2, SPE-G and SPE-H were modelled onto the superimposed structurally conserved regions of SEA, SEB and SPE-C. The models showed that in all three proteins, the 2 amino acid side chains of the COOH-terminal primary zinc binding motif are in close proximity to a third potential zinc ligand to build a zinc binding site, similar to the zinc binding site observed in SEA and SPE-C.

The zinc binding residues in SPE-C are H167, H201, D203, and it is thought that H81 from the HLA-DR1 β-chain binds to the same zinc cation to form a regular tetrahedral complex. The two ligands of the primary zinc binding motif, H201 and D203 are located on the β12 strand, which is part of the β-grasp motif, a common structural domain of superantigens. The third ligand, H167, comes from the β10 strand (Roussel et al. 1997).

In the model of SPE-G three potential zinc binding ligands (H167, H202 and D204) are located at corresponding positions. In the SMEZ-2 and the SPE-H models, the two corresponding p12 residues are H202, D204 and H198, D200, respectively. The third ligand in SPE-H (D1160) and in SMEZ-2 (H162) comes from the β9 strand and is most similar to H187 in SEA. It has been shown from crystal structures that H167 of SPE-C and H187 of SEA are spatially and geometrically equivalent sites (Scad et al. 1997, Embo J 14 no 14:3292-301; Roussel et al. 1997).

All superantigens examined so far, except SPE-C, bind to a conserved motif in the MHC class II α1-domain. In SEB and TSST, hydrophobic residues on the loop between the β1 and β2 strand project into a hydrophobic depression in the MHCII α1-domain. This loop region has changed its character in SPE-C, where the hydrophobic residues (F44, L45, Y46 and F47 in SEB) are substituted by the less hydrophobic residues T33, T34 and H35. A comparison of this region on the computer generated models revealed that the generic HLA-DR1 α-chain binding site might also be missing. As the loop regions are generated by random choice, no conclusions can be drawn from their conformation in the models. However, in none of the three models does the β1-β2-loop have the required hydrophobic features observed in SEB and TSST Swaminathan, S. et al., Nature 359, No. 6398:801-6 (1992), Acharya et al., Nature 367, No. 6458: 94-7 (1994). The residues are I25, D26, F27, K28, T29 and S30 in SMEZ-2, T31, T32, N33, S34 in SPE-G and K28, N29, S30, P31, D32, I33, V34 and T35 in SPE-H.

SMEZ-2 differs from SMEZ in only 17 amino acids. In the model of SMEZ-2 with the position of those 17 residues, most of the exchanges are located on loop regions, most significantly on the β5-β6 loop with 5 consecutive residues replaced. The potential zinc binding site and the β1-β2 loop are not affected by the replaced amino acids.

The TcR Vβ specificity differs between SMEZ and SMEZ-2 by one Vβ. SMEZ strongly stimulates Vβ2 T cells, but SMEZ-2 does not (Table 2). One or more of the 17 exchanged residues in SMEZ/SMEZ-2 may therefore be directly involved in TcR binding. The exact position of the TcR binding site can not be predicted from the model as several regions have been implicated in TcR binding for different toxins. Crystal structures of SEC2 and SEC3, complexed with a TcR P-chain indicated the direct role of several residues located on α2, the β2-β3 loop, the β4-β5 loop and α4 (Fields et al. 1996 Nature 384 no 6605:188-92). On the other hand, binding of TSST to the TcR involves residues from α4, the β7-β8 loop and the α4-β9 loop (Acharya et al. 1994, Nature 367 no 6548:94-7). The SMEZ-2 model shows 3 residues, which may contribute to TcR binding. In SMEZ, Lys is exchanged for Glu at position 80 and Thr is exchanged for Ile at position 84, both on the β4-β5 loop. On the COOH-terminal end of the α4 helix, Ala is replaced by Ser at position 143.

The results from the computer modelled protein structures suggest that all 4 toxins, SMEZ, SMEZ-2, SPE-G and SPE-H, might bind to the HLA-DR1 β-chain in a zinc dependent fashion, similar to SEA and SPE-C, but might not be able to interact with the HLA-DR1 α-site, a situation that has so far only been observed with SPE-C (Roussel et al. 1997; Li et al. 1997).

To find out whether or not zinc is required for binding of the toxins to MHC class II, a binding assay was performed using human LG-2 cells (which are MHC class II expressing cells homozygous for HLA-DR1). Direct binding of $^{125}$I-labeled toxins was completely abolished in the presence of 1 mM EDTA (FIG. 9, Table 3). When 2 mM ZnCl$_2$ was added, binding to the LG-2 cells could be restored completely. These results show that the toxins bind in a zinc dependent mode, most likely to the HLA-DR1 β-chain similar to SEA and SPE-C. However, it does yet not exclude the possibility of an additional binding to the HLA-DR1 α-chain.

TABLE 3

BINDING AFFINITIES AND ZINC DEPENDENCIES
FOR SUPERANTIGENS TO HUMAN CLASS II

| TOXIN | MHC CLASS II BINDING kd [nM] | ZINC DEPENDENCY |
|---|---|---|
| SEA | 36/1000 | ++ |
| SEB | 340 | − |
| TSST | 130 | − |
| SPE-C | 70 | ++ |
| SMEZ | 65/1000 | ++ |
| SMEZ-2 | 25/1000 | ++ |
| SPE-G | 16/1000 | ++ |
| SPE-H | 37/2000 | ++ |

The binding affinities of the toxins to MHC class II were determined by Scatchard analysis using LG-2 cells. Zinc dependency was determined by binding of recombinant toxins to LG-2 cells in the presence and absence of EDTA, as described in the Materials and Methods section.

The biphasic binding of SEA to HLA-DR1 can be deduced from Scatchard analysis. It shows that SEA possesses a high affinity binding site of 36 nM (which is the zinc dependent β-chain binding site) and a low affinity binding site of 1 µM (α-chain binding site). On the other hand, only one binding site for HLA-DR1 was deduced from Scatchard analysis with SEB, TSST and SPE-C, respectively (Table 3).

Therefore, Scatchard analysis was performed with radiolabeled rSMEZ, rSMEZ-2, rSPE-G and rSPE-H using LG-2 cells. All four toxins showed multiphasic curves with at least 2 binding sites on LG-2 cells, a high affinity site of 15-65 nM and a low affinity site of 1-2 µM (FIG. 10, Table 3).

In a further attempt to determine the orientation of the toxins on MHC class II competition binding experiments were performed. The recombinant toxins and reference toxins (rSEA, rSEB, rSPE-C and rTSST) were radiolabeled and tested with excess of unlabeled toxin for binding to LG-2 cells. The results are summarized in FIG. 11. Both, rSEA and rSPE-C, inhibited binding of labeled rSMEZ, rSMEZ-2, rSPE-G and rSPE-H, respectively. However, rSPE-C only partially inhibited binding (50%) of the labeled rSMEZ-2 (FIG. 12). Recombinant SEB did not compete with any other toxin, even at the highest concentration tested. Recombinant TSST was only slightly competitive against $^{125}$I-labeled rSMEZ, rSMEZ-2 and rSPE-G, respectively, and did not inhibit rSPE-H binding at all.

Reciprocal competition experiments were performed. Recombinant SMEZ, rSMEZ-2 and rSPE-H prevented [125]I-rSEA from binding to LG-2 cells. However, only partial competition (50%) was observed even at the highest toxin concentrations (10,000 fold molar excess). Recombinant SPE-G did not prevent binding of [125]I-rSEA and [125]I-rTSST binding was only partially inhibited by rSMEZ, rSMEZ-2 and rSPE-H, but not by rSPE-G. Significantly, none of the toxins inhibited [125]I-rSEB binding, even at the highest concentration tested.

In a further set of competition binding experiments, rSMEZ, rSMEZ-2, rSPE-G and rSPE-H were tested for competition against each other. Both, rSMEZ and rSMEZ-2 competed equally with each other and also prevented binding of labeled rSPE-G and rSPE-H. In contrast, rSPE-G and rSPE-H did not inhibit any other toxin binding suggesting that these toxins had the most restricted subset of MHC class II molecules, which represent specific receptors.

Section B: Genotyping

Genotyping of S. pyogenes Isolates

Purified genomic DNA from all Str Pyrogenes isolates was used for PCR with specific primers for the smez, spe-g and spe-h genes as described above and by Proft (1999). In addition, a primer pair specific to a DNA region encoding the 23S, rRNA, oligo 23rRNA forward (SEQ ID NO:18) (GC-TATTTCGGAGAGAACCAG) and oligo 23rRNA reverse (SEQ ID NO:19) (CTGAAACATCTAAGTAGCTG) was designed and used for PCR as a positive control.

Southern Blot Analysis

About 5 µg of genomic DNA was digested using restriction enzyme HindIII (GIBCO) and loaded onto a 0.7% agarose gel. The DNA was transferred from the gel to a Hybond-N+ nylon membrane (Amersham) as described by Maniatis (1989). A 640 bp DNA fragment of the smez-2 gene was radiolabeled using the RadPrime Labeling System (GIBCO) and a $^{32}$P-dCTP (NEN). The nylon blots were hybridized with the radiolabeled probe in 2×SSC, 0.5% SDS, 5× Denhards overnight at 65° C. After washing twice in 0.2×SSC, 0.1% SDS at 65° C. the blots were analysed on a Storm PhosphorImager.

Results

PCR based genotyping was performed in order to determine the frequency of the genes smez, spe-g and spe-h in streptococcal isolates (Table 4). The PCR primers for smez were designed to anneal with both genes, semz and smez-2. 103 isolates were collected between 1976 and 1998 from varying sites in patients with varying infections, although the majority were from sore throats. They comprised 94 group A Streptococcus (GAS) and 9 non-GAS, which were S. agalactiae (group B), S. equis (group C) and Streptococcus spp (group C). There are 25 distinct M/emm types represented among the GAS isolates, 13 isolates are M non-typable (MNT) and in 2 cases the M type is unknown. The analysis was undertaken blinded to the details of each isolate and 2 duplicate isolates were included (95/31 and 4202) to demonstrate the reproducibility of the testing procedure. The isolates are listed in 2 groups. Group 1 contained isolates collected within a large time frame (1976 to 1996). Group 2 comprised of isolates collected within a short time (1998).

All of the 9 non-GAS isolates (belonging to groups B, C and G) were negative for the tested sag genes. The frequencies for smez, spe-g and spe-h within the GAS isolates were 95.6%, 100% and 23.9% respectively. A correlation between a certain M/emm type and the presence of the spe-h gene could not be established. The deficiency in this current set was that only 5M/emm types were represented by more than one isolate. The most frequent serotype was M/emm 12 with 13 isolates, from which 7 were positive and 6 were negative for spe-h suggesting genetic diversity within the M/emm12 strain. In contrast, all 12 tested NZ1437/M89 isolates were negative for spe-h.

The high frequencies of smez and spe-g is of particular interest as this has not been described for any other streptococcal sag gene thus far. Other spe genes, like speA, speC and ssa are found at much lower frequencies and horizontal gene transfer might explain the varying frequencies of these genes in different strains. In contrast, both smez and spe-g were found in virtually all tested GAS isolates. Only 4 GAS isolates (11152, 11070, 94/229 and 11610) tested negative for smez. These were PT2612, emm65, M49 and emm57. Southern hybridisation was performed to find out if the negative PCR results were due to lack of the smez gene or to lack/alteration of the primer binding site(s). HindIII digested genomic DNA of selected streptococcal isolates was probed with a 640 bp radiolabeled smz-2 PCR fragment (FIG. 13). The smez gene is located on a 1953 bp HindIII fragment of about 4 kb (fragment B), but not to the SMEZ bearing fragment A (lanes 4, 6, 9, 10). In addition, the smez probe bound to a second DNA fragment of about 4.2 kb (fragment C) in isolate 11152 (lane 4). In the M1 reference strain (lane 1) and in isolate 4202 (lane 8) the smez probe also bound to fragment B, in addition to fragment A. Fragment B in the M1 strain contains a 180 bp region that shares 97% sequence homology with the 3' end of the smez gene. These results suggest that the 4 PCR negative isolates possess a truncated smez gene or a smez-like sequence, but not a complete smez gene.

TABLE 4

Group 1: Isolates collected between 1976 and 1996

| Strain No. | Group | M/emm | Site | Disease | Rib.DNA | Spe-g | Spe-h | Smez | Vβ8 |
|---|---|---|---|---|---|---|---|---|---|
| FP 1943 | A | M53 | ts | ST | + | + | − | + | − |
| FP 2658 | A | M59 | ts | ST | + | + | − | + | − |
| FP 4223 | A | M80 | ts | ST | + | + | − | + | + |
| FP 5417 | A | M41 | ts | ST | + | + | − | + | + |
| FP 5847 | A | M1 | ts | ST | + | + | − | + | + |
| FP 5971 | A | M57 | ts | ST | + | + | + | + | − |
| 1/5045 | A | M4 | ts | ST | + | + | − | + | + |
| 79/1575 | A | M1 | ts | Tcarriage | + | + | + | + | + |
| 81/3033 | A | M12 | ts | ST | + | + | + | + | + |
| 82/20 | A | M4 | sk | ulcer | + | + | − | + | + |
| 82/532 | A | M12 | ts | ST | + | + | + | + | + |
| 82/675 | A | NZ1437 § | ws | wound | + | + | − | + | + |
| 84/141 | A | M12 | ts | ST | + | + | + | + | + |
| 84/1733 | A | M4 | ts | ST | + | + | − | + | + |
| 84/781 | A | NZ1437 § | ts | ST | + | + | − | + | + |
| 85/1 | A | M12 | ts | ST | + | + | + | + | + |
| 85/167 | A | M12 | ts | ST | + | + | + | + | + |
| 85/314 | A | NZ1437 § | ws | wound | + | + | − | + | + |
| 85/437 | A | M81 | ws | inf eczema | + | + | − | + | + |
| 85/722 | A | n.d. | ? | ? | + | + | − | + | − |
| 86/435 | A | M4 | ts | RF | + | + | − | + | + |
| 87/169 | A | M12 | ts | ST | + | + | + | + | + |
| 87/19 | A | M12 | ts | ST | + | + | + | + | + |
| 87/781 | A | M12 | ts | ST | + | + | − | + | + |
| 88/627 | A | M12 | sk | wound | + | + | − | + | − |
| 89/22 | A | M12 | ts | fever | + | + | − | + | + |
| 89/25 | A | M12 | ur | erysipelas | + | + | + | + | + |
| 89/26 | A | M1 | ts | AGN | + | + | − | + | + |
| 89/54 | A | NZ1437 § | ts | ST | + | + | − | + | + |
| 90/306 | A | M5 | ear | otorrhoea | + | + | − | + | + |
| 90/424 | A | M4 | ts | ST | + | + | − | + | + |
| 91/542 | A | M12 | ts | ST | + | + | − | + | + |
| 94/11 | A | NZ1437 § | ps | abscess | + | + | − | + | + |
| 94/229 | A | M49 | hvs | endometr. | + | + | + | − | − |
| 94/330 | A | M4 | ts | SF | + | + | − | + | + |
| 94/354 | A | M12 | ts | ST | + | + | − | + | + |
| 94/384 | A | M4 | sk | wound | + | + | − | + | + |
| 94/712 | A | NZ1437 § | ws | cellulitis | + | + | − | + | + |
| 95/127 | A | NZ1437 § | bc | cellulitis | + | + | − | + | + |
| 95/31 | lA | NZ1437 § | ws | abscess | + | + | − | + | + |
| 95/31(2) | lA | NZ1437 § | ws | abscess | + | + | − | + | + |
| 95/361 | A | NZ1437 § | ps | abscess | + | + | − | + | + |
| 96/1 | A | n.d. | ? | ? | + | + | − | + | + |
| 96/364 | A | NZ1437 § | be | burns | + | + | − | + | + |
| 96/551 | A | M4 | eye | eye infect | + | + | − | + | + |
| 96/610 | A | M4 | ts | SF | + | + | − | + | + |
| D21 | A | M1 | ts | Tcarriage | + | + | − | + | + |
| RC4063 | C | — | ts | ST | + | − | − | − | − |
| SP9205 | C | — | ts | ST | + | − | − | − | − |
| NI6174 | G | — | ts | ST | + | − | − | − | − |
| NI6192 | B | — | ts | ST | + | − | − | − | − |
| VC4141 | G | — | ts | ST | + | − | − | − | − |

Group 2: Isolates collected in 1998

| Strain No. | student ID | group | M/emm | site | disease | rib.DNA | spe-g | spe-h | smez | Vβ8 |
|---|---|---|---|---|---|---|---|---|---|---|
| 4202 * | 3310 | A | NZ5118II | ts | ST | + | + | − | + | + |
| 4202(2) | 3310 | A | NZ5118II | ts | ST | + | + | − | + | + |
| 9606 | 2252 | A | MNT | ts | ST | + | + | − | + | − |
| 9639 | 2184 | A | MNT | ts | ST | + | + | + | + | + |
| 9779 | 3230 | A | emm56 | ts | ST | + | + | − | + | + |
| 9893 | 6144 | A | PT180 | ts | ST | + | + | + | + | + |

TABLE 4-continued

| | | | | | | | | | | |
|---|---|---|---|---|---|---|---|---|---|---|
| 9894 | 6564 | A | emm59 | ts | ST | + | + | − | + | + |
| 10019 | 6264 | A | emm44 | ts | ST | + | + | + | + | − |
| 10028 | 9366 | A | emm41 | ts | ST | + | + | − | + | + |
| 10134 | 1880 | A | ST4547 | ts | ST | + | + | − | + | − |
| 10303 | 3564 | A | emm59 | ts | ST | + | + | − | + | − |
| 10307 | 4850 | A | NZ5118Π | ts | ST | + | + | − | + | + |
| 10438 | 4904 | A | ST3018 | ts | ST | + | + | − | + | + |
| 10463 | TSP | A | emm49 | ts | ST | + | + | − | + | − |
| 10649 | 11510 | A | ST2267 | ts | ST | + | + | − | + | + |
| 10730 | 11503 | A | MNT | ts | ST | + | + | − | + | − |
| 10742 | 3374 | A | ST809 | ts | ST | + | + | − | + | + |
| 10761 | 3254 | A | MNT | ts | ST | + | + | − | + | − |
| 10763 | 6614 | PT 3875 | ts | ST | + | + | − | + | − | 10782 |
| 4850 | A | MNT | ts | ST | + | + | + | + | + | + |
| 10791 | 10290 | A | MNT | ts | ST | + | + | + | + | + |
| 10792 | 10308 | A | MNT | ts | ST | + | + | + | + | − |
| 10846 | 8854 | A | NZ1437 § | ts | ST | + | + | − | + | + |
| 10902 | 6264 | A | NZ5118Π | ts | ST | + | + | − | + | + |
| 10989 | 5194 | A | PT2841 | ts | ST | + | + | − | + | − |
| 11070 | 1434 | A | emm65 | ts | ST | + | + | + | − | − |
| 11072 | 1880 | A | ST4547 | ts | ST | + | + | − | + | − |
| 11083 | 4538 | A | MNT | ts | ST | + | + | − | + | − |
| 11093 | 9791 | A | MNT | ts | ST | + | + | + | + | + |
| 11152 | 2030 | A | PT2612 | ts | ST | + | + | + | − | − |
| 11222 | 4928 | A | NZ5118Π | ts | ST | + | + | + | + | + |
| 11227 | 8854 | A | emm14 | ts | ST | + | + | − | + | − |
| 11244 | 2252 | A | ST4547 | ts | ST | + | + | − | + | − |
| 11276 | 4524 | A | MNT | ts | ST | + | + | − | + | − |
| 11299 | 2950 | A | emm80 | ts | ST | + | + | − | + | + |
| 11574 | 3186 | A | ST809 | ts | ST | + | + | − | + | + |
| 11580 | 3280 | A | emm53 | ts | ST | + | + | − | + | − |
| 11610 | 2424 | A | emm57 | ts | ST | + | + | + | − | − |
| 11646 | 1880 | A | ST4547 | ts | ST | + | + | − | + | − |
| 11681 | 3564 | A | emm12 | ts | ST | + | + | − | + | + |
| 11686 | 5528 | A | PT5757 | ts | ST | + | + | − | + | + |
| 11745 | 12397 | A | emm59 | ts | ST | + | + | − | + | − |
| 11789 | 1568 | A | MNT | ts | ST | + | + | − | + | − |
| 11802 | 3266 | A | MNT | ts | ST | + | + | − | + | − |
| 11869 | 2950 | A | ST4547 | ts | ST | + | + | − | + | − |
| 11961 | 4916 | A | MNT | ts | ST | + | + | − | + | − |
| 12015 | 12373 | A | emm59 | ts | ST | + | + | + | + | − |
| 7625 | 8215 | B | — | ts | ST | + | − | − | − | − |
| 8011 | 3238 | B | — | ts | ST | + | − | − | − | − |
| 10388 | 1653 | G | — | ts | ST | + | − | − | − | − |
| O12633 | 5395 | B | — | ts | ST | + | − | − | − | − |

Genotyping of streptococcal isolates. The isolates were collected between 1976 and 1996 (group 1) and in 1998 (group 2) from patients with varying diseases. The results are based on PCR analysis using purified genomic DNA and specific primers for each of the sag genes.

The non Gas are: B, *S. agalactiae*; C, *S. equis*; G, *Streptococcus* spp.

MNT, M non typable: ts, throat site; ws, wound site; sk, skin; ps, pus site; hvs, high vaginal site; bc, blood culture; ST, sore throat; SF, scarlet fever; RF, rheumatic fever; AGN, acute glomerulonephritis; T carriage, throat carriage.

* and ¦, duplicate isolates; §, recently assigned as M89; Π, recently assigned as M92.

INDUSTRIAL APPLICATION

The superantigens of the invention, polynucleotides which encode them and antibodies which bind them have numerous applications. A number of these are discussed above (including Streptococci subtyping, diagnostic applications and therapeutic applications) but it will be appreciated that these are but examples. Other applications will present themselves to those skilled in the art and are in no way excluded from the scope of the invention.

It will also be appreciated that the foregoing examples are illustrations of the invention. The invention may be carried out with the numerous variations and modifications as will be apparent to those skilled in the art. For example, one or more deletions, insertions and/or substitutions relative to the corresponding natural superantigen, provided that the superantigen activity is retained. Likewise there are many variations in the way in which the invention can be used in other aspects of it.

REFERENCES

Marrack, P., and J. Kappler. 1990. The staphylococcal enterotoxins and their relatives. *Science* 248:705-711.

Huber, B. T., P. N. Hsu, and N. Sutkowski. 1996. Virus-encoded superantigens. *Microbiol. Rev.* 60, no. 3:473-82.

Alouf, J. E., H. Knoell, and W. Koehler. 1991. The family of mitogenic, shock-inducing and superantigenic toxins from staphylococci and streptococci. Sourcebook of bacterial protein toxins., eds. J. E. Alouf and J. H. Freer. Academic Press, San Diego. 367-414 pp.

Betley, M. J., D. W. Borst, and L. B. Regassa. 1992. Staphylococcal enterotoxins, toxic shock syndrome toxin and streptococcal exotoxins: a comparative study of their molecular biology. *Chem. Immunol.* 55:1-35.

Ren, K., J. D. Bannan, V. Pancholi, A. L. Cheung, J. C. Robbins, V. A. Fischetti, and J. B. Zabriskie. 1994. Characterization and biological properties of a new staphylococcal exotoxin. *J. Exp. Med.* 180, no. 5:1675-83.

Munson, S. H., M. T. Tremaine, M. J. Betley, and R. A. Welch. 1998. Identification and Characterization Of Staphylococcal Enterotoxin Types G and I From *Staphylococcus Aureus*. *Infect. Immun.* 66, no. 7:3337-3348.

Herman, A., J. W. Kappler, P. Marrack, and A. M. Pullen. 1991. Superantigens: mechanism of T-cell stimulation and role in immune responses. *Annu. Rev. Immunol.* 9:745-772.

Janeway, C. J., J. Yagi, P. J. Conrad, M. E. Katz, B. Jones, S. Vroegop, and S. Buxser. 1989. T-cell responses to Mls and to bacterial proteins that mimic its behavior. *Immunol. Rev.* 107:61-68.

Fast, D. J., P. M. Schlievert, and R. D. Nelson. 1989. Toxic shock syndrome-associated staphylococcal and streptococcal pyrogenic toxins are potent inducers of tumor necrosis factor production. *Infect. Immun.* 57, no. 1:291-4.

Kotzin, B. L., D. Y. Leung, J. Kappler, and P. Marrack. 1993. Superantigens and their potential role in human disease. *Adv. Immunol.* 54, no. 99:99-166.

Bohach, G. A., D. J. Fast, R. D. Nelson, and P. M. Schlievert. 1990. Staphylococcal and streptococcal pyrogenic toxins involved in toxic shock syndrome and related illnesses. *Crit. Rev. Microbol.* 17, no. 4:251-72.

Weeks, C. R., and J. J. Ferretti. 1986. Nucleotide Sequence of the Type A Streptococcal Exotoxin (Erythrogenic Toxin) Gene from *Streptococcus pyogenes* Bacteriophage T12. *Infect. Immun.* 52:144-150.

Goshorn, S. C., G. A. Bohach, and P. M. Schlievert. 1988. Cloning and characterization of the gene, speC, for pyrogenic exotoxin type C from *Streptococcus pyogenes*. *Mol. Gen. Genet.* 212, no. 1:66-70.

Mollick, J. A., G. G. Miller, J. M. Musser, R. G. Cook, D. Grossman, and R. R. Rich. 1993. A novel superantigen isolated from pathogenic strains of *Streptococcus pyogenes* with aminoterminal homology to staphylococcal enterotoxins B and C. *J. Clin. Invest.* 92, no. 2:710-9.

Van Den Busche, R. A., J. D. Lyon, and G. A. Bohach. 1993. Molecular evolution of the staphylococcal and streptococcal pyrogenic toxin gene family. *Mol. Phylogenet. Evol.* 2:281-292.

Dellabona, P., J. Peccoud, J. Kappler, P. Marrack, C. Benoist, and D. Mathis. 1990. Superantigens interact with MHC class II molecules outside of the antigen groove. *Cell* 62, no. 6:1115-21.

Fraser, J. D. 1989. High-affinity binding of staphylococcal enterotoxins A and B to HLA-DR. *Nature* 339, no. 6221:221-3.

Fleischer, B., and H. Schrezenmeier. 1988. T cell stimulation by staphylococcal enterotoxins. Clonally variable response and requirement for major histocompatibility complex class II molecules on accessory or target cells. *J. Exp. Med* 167, no. 5:1697-707.

Mollick, J. A., R. G. Cook, and R. R. Rich. 1989. Class II MHC molecules are specific receptors for *staphylococcus* enterotoxin A. *Science* 244, no. 4906:817-20.

Schad, E. M., I. Zaitseva, V. N. Zaitsev, M. Dohlsten, T. Kalland, P. M. Schlievert, D. H. Ohlendorf, and L. A. Svensson. 1995. Crystal structure of the superantigen staphylococcal enterotoxin type A. *EMBO J.* 14, no. 14:3292-301.

Swaminathan, S., W. Furey, J. Pletcher, and M. Sax. 1992. Crystal structure of staphylococcal enterotoxin B, a superantigen. *Nature* 359, no. 6398:801-6.

Papageorgiou, A. C., K. R. Acharya, R. Shapiro, E. F. Passalacqua, R. D. Brehm, and H. S. Tranter. 1995. Crystal structure of the superantigen enterotoxin C2 from *Staphylococcus aureus* reveals a zinc-binding site. *Structure* 3, no. 8:769-79.

Sundstrom, M., L. Abrahmsen, P. Antonsson, K. Mehindate, W. Mourad, and M. Dohlsten. 1996. The crystal structure of staphylococcal enterotoxin type D reveals Zn2+-mediated homodimerization. *EMBO J.* 15, no. 24:6832-40.

Acharya, K. R., E. F. Passalacqua, E. Y. Jones, K. Harlos, D. I. Stuart, R. D. Brehm, and H. S. Tranter. 1994. Structural basis of superantigen action inferred from crystal structure of toxic-shock syndrome toxin-1. *Nature* 367, no. 6458:94-7.

Roussel, A., B. F. Anderson, H. M. Baker, J. D. Fraser, and E. N. Baker. 1997. Crystal structure of the streptococcal superantigen SPE-C: dimerization and zinc binding suggest a novel mode of interaction with MHC class II molecules. *Nat. Struct. Biol.* 4, no. 8:635-43.

Kim, J., R. G. Urban, J. L. Strominger, and D. C. Wiley. 1994. Toxic shock syndrome toxin-1 complexed with a class II major histocompatibility molecule HLA-DR1. *Science* 266, no. 5192:1870-4.

Hurley, J. M., R. Shimonkevitz, A. Hanagan, K. Enney, E. Boen, S. Malmstrom, B. L. Kotzin, and M. Matsumura. 1995. Identification of class II major histocompatibility complex and T cell receptor binding sites in the superantigen toxic shock syndrome toxin 1. *J. Exp. Med.* 181, no. 6:2229-35.

Seth, A., L. J. Stern, T. H. Ottenhoff, I. Engel, M. J. Owen, J. R. Lamb, R. D. Klausner, and D. C. Wiley. 1994. Binary and ternary complexes between T-cell receptor, class II MHC and superantigen in vitro. Source (Bibliographic Citation): *Nature* 369, no. 6478:324-7.

Li, P. L., R. E. Tiedemann, S. L. Moffat, and J. D. Fraser. 1997. The superantigen streptococcal pyrogenic exotoxin C (SPE-C) exhibits a novel mode of action. *J. Exp. Med.* 186, no. 3:375-83.

Hudson, K. R., R. E. Tiedemann, R. G. Urban, S. C. Lowe, J. L. Strominger, and J. D. Fraser. 1995. Staphylococcal enterotoxin A has two cooperative binding sites on major histocompatibility complex class II. *J. Exp. Med.* 182, no. 3:711-20.

Kozono, H., D. Parker, J. White, P. Marrack, and J. Kappler. 1995. Multiple binding sites for bacterial superantigens on soluble class II MHC molecules. *Immunity* 3, no. 2:187-96.

Tiedemann, R. E., and J. D. Fraser. 1996. Cross-linking of MHC class II molecules by staphylococcal enterotoxin A is essential for antigen-presenting cell and T cell activation. *J. Immunol.* 157, no. 9:3958-66.

Braun, M. A., D. Gerlach, U. F. Hartwig, J. H. Ozegowski, F. Romagne, S. Carrel, W. Kohler, and B. Fleischer. 1993. Stimulation of human T cells by streptococcal "superantigen" erythrogenic toxins (scarlet fever toxins). *J. Immunol.* 150, no. 6:2457-66.

Kline, J. B., and C. M. Collins. 1997. Analysis of the interaction between the bacterial superantigen streptococcal pyrogenic exotoxin A (SpeA) and the human T-cell receptor. *Mol. Microbiol.* 24, no. 1:191-202.

Fleischer, B., A. Necker, C. Leget, B. Malissen, and F. Romagne. 1996. Reactivity of mouse T-cell hybridomas expressing human Vbeta gene segments with staphylococcal and streptococcal superantigens. *Infect. Immun.* 64, no. 3:987-94.

Toyosaki, T., T. Yoshioka, Y. Tsuruta, T. Yutsudo, M. Iwasaki, and R. Suzuki. 1996. Definition of the mitogenic factor (MF) as a novel streptococcal superantigen that is different from streptococcal pyrogenic exotoxins A, B, and C. *Eur. J. Immunol.* 26, no. 11:2693-701.

Kamezawa, Y., T. Nakahara, S. Nakano, Y. Abe, J. Nozaki-Renard, and T. Isono. 1997. Streptococcal mitogenic exotoxin Z, a novel acidic superantigenic toxin produced by a T1 strain of *Streptococcus pyogenes*. *Infect. Immun.* 65, no. 9:3828-33.

Hudson, K. R., H. Robinson, and J. D. Fraser. 1993. Two adjacent residues in Staphylococcal enterotoxins A an E determine Tcell receptor V beta specificity. *J. Exp. Med.* 177:175-185.

Kraulis, P. J. 1991. MOLSCRIPT": a program to produce both detailed and schematic plots of protein structures. *J. Appl. Critallography* 24:946-950.

Cunningham, B. C., P. Jhurani, P. Ng, and J. A. Wells. 1989. Receptor and Antibody epitopes in human growth hormone identified by homologue scanning mutagenesis. *Science* 243:1330-1336.

Fields, B. A., E. L. Malchiodi, H. Li, X. Ysern, C. V. Stauffacher, P. M. Schlievert, K. Karjalainen, and R. A. Mariuzza. 1996. Crystal structure of a T-cell receptor beta-chain complexed with a superantigen [see comments]. *Nature* 384, no. 6605:188-92.

Wen, R., G. A. Cole, S. Surman, M. A. Blackman, and D. L. Woodland. 1996. Major histocompatibility complex class II-associated peptides control the presentation of bacterial superantigens to T cells. *J. Exp. Med.* 183, no. 3:1083-92.

Thibodeau, J., I. Cloutier, P. M. Lavoie; N. Labrecque, W. Mourad, T. Jardetzky, and R. P. Sekaly. 1994. Subsets of HLA-DR1 molecules defined by SEB and TSST-1 binding. *Science* 266, no. 5192:1874-8.

Abe, J., B. L. Kotzin, K. Jujo, M. E. Melish, M. P. Glode, T. Kohsaka, and D. Y. Leung. 1992. Selective expansion of T cells expressing T-cell receptor variable regions V beta 2 and V beta 8 in Kawasald disease. *PNAS* 89, no. 9:4066-70.

Kawasaki, T. 1967. Acute febrile mucocutaneous syndrome with lymphoid involvement with specific desquamation of the fingers and toes in children. *Jpn. J. Allergol.* 16:178.

Leung, D. Y., R. C. Giorno, L. V. Kazemi, P. A. Flynn, and J. B. Busse. 1995. Evidence for superantigen involvement in cardiovascular injury due to Kawasaki syndrome. *J. Immunol.* 155, no. 10:5018-21.

Cockerill, F. R., R. L. Thompson, J. M. Musser, P. M. Schlievert, J. Talbot, K. E. Holley, W. S. Harmsen, D. M. Ilstrup, P. C. Kohner, M. H. Kim, B. Frankfort, J. M. Manahan, J. M. Steckelberg, F. Roberson, and W. R. Wilson. 1998. Molecular, Serological, and Clinical Features Of 16 Consecutive Cases Of Invasive Streptococcal Disease. *Clin. Infect. Dis.* 26, no. 6:1448-1458.

Kapur, V., K. B. Reda, L. L. Li, L. J. Ho, R. R. Rich, and J. M. Musser. 1994. Characterization and distribution of insertion sequence IS1239 in *Streptococcus pyogenes*. *Gene* 150, no. 1:135-40.

T. Proft, S. L. Moffatt, C. J. Berkahn, and J. D. Fraser (1999). Identification and characterisation of novel superantigens from *Streptoccocus pyogenes*. *Journal of Experimental Medicine* 189, No. 1:89-102.

T. Maniatis, E. F. Fritsch, and J. Sambrook. (1989). Molecular cloning: a laboratory manual. Cold Spring Harbour Laboratory, Cold Spring Harbour, N.Y., USA.

B. A. Roe, S. P. Linn, L. Song, X. Yuan, S. Clifton, M. McShan and J. Ferretti, (1999). *Str. Pyogenes* M1 genome sequencing project at Oklahoma University. Web: http://www.genome.ou.edu.

---

The invention claimed is:

1. A purified superantigen comprising the amino acid sequence of SEQ ID NO:20.

2. The purified superantigen of claim 1, wherein the superantigen has the amino acid sequence of SEQ ID NO:20.

3. The purified superantigen of claim 1, wherein the superantigen comprises the amino acid sequence of SEQ ID NO:2.

4. The purified superantigen of claim 3, wherein the superantigen has the amino acid sequence of SEQ ID NO:2.

5. The purified superantigen of claim 3, wherein the superantigen is encoded by the nucleotide sequence of SEQ ID NO:1.

6. A method of subtyping *Streptococci* comprising:
providing a *Streptococci* sample to be tested;
determining whether or not a superantigen SMEZ-2 containing the amino acid sequence of SEQ ID NO:20 is present in said sample; and
subtyping the *Streptococci* on the basis of whether or not SMEZ-2 is present.

7. The method of claim 6, wherein the superantigen SMEZ-2 has the amino acid sequence of SEQ ID NO:2.

* * * * *

UNITED STATES PATENT AND TRADEMARK OFFICE
CERTIFICATE OF CORRECTION

PATENT NO. : 7,491,402 B2  Page 1 of 3
APPLICATION NO. : 10/997690
DATED : February 17, 2009
INVENTOR(S) : John David Fraser et al.

It is certified that error appears in the above-identified patent and that said Letters Patent is hereby corrected as shown below:

AMENDMENTS TO THE DRAWINGS:

The attached replacement sheet of drawings includes changes to FIG. 1 and replaces the original sheet including FIG. 1.
As shown in revised FIG. 1, inadvertent errors in the amino acid sequences shown in original FIG. 1 have been corrected.

AMENDMENTS TO THE SPECIFICATION:

Please replace the paragraph beginning at Column 3, Line 55 with the following amended paragraph:

The most significant difference between SMEZ and SMEZ-2 is an exchanged pentapeptide sequence at position 96-100, where the EEPMS (SEQ ID NO:23) sequence of SMEZ is converted to KTSIL KTSIP (SEQ ID NO:[[24]] 25) in SMEZ-2 (Fig. 1   Fig. 2). A second difference is at position 111-112, where an RR dipeptide is exchanged for GK in SMEZ-2. The remaining 10 different residues are spread over almost the entire primary sequence.

Please replace the paragraph beginning at Column 12, Line 32 with the following amended paragraph:

The most significant different between SMEZ and SMEZ-2 is an exchanged pentapeptide sequence at position 96-100, where the EEPMS (SEQ ID NO:23) sequence of SMEZ is converted to KTSIL KTSIP (SEQ ID NO:[[24]] 25) in SMEZ-2 (Fig. 1   Fig. 2). A second cluster is at position 111-112, where an RR dipeptide is exchanged for GK in SMEZ-2. The remaining 10 different residues are spread over almost the entire primary sequence.

Signed and Sealed this

Twenty-first Day of December, 2010

David J. Kappos
*Director of the United States Patent and Trademark Office*

CERTIFICATE OF CORRECTION (continued)
U.S. Pat. No. 7,491,402 B2

Please replace the paragraph beginning at Column 14, Line 3 with the following amended paragraph:

The half maximal response for rSPE-G and rSPE-H was 2 pg/ml and 50 pg/ml, respectively. No activity was detected at less than 0.02 pg/ml and 0.1 pg/ml, respectively. Both toxins are therefore less potent than rSPE-C. Recombinant SMEZ was similar in potency to rSPE-C, with a P50% value of 0.08 pg/ml and no detectable proliferation at less than 0.5 fg/ml. Recombinant SMEZ-2 showed the strongest mitogenic potency of all toxins tested or, as far as can be determined, described elsewhere. The P50% value of 0.02 pg/ml and rSMEZ-2 was still active at less than 0.1 pg/ml fg/ml. All P50% values are summarized in Table 1.

```
SMEZ    --------  --------  LEVDNNSLLR  NIYSTIVYEY  SDTVIDFKTS   30
SMEZ-2  --------  --------  LEVDNNSLLR  NIYSTIVYEY  SDIVIDFKTS   30
SPE-J   --------  --------  ----------  ----------  ----------
SPE-C   --------  ----DSKK  DISNVKSDLL  YAYTITPYDY  KDCRVNFSTT   34
SPE-G   --------  ------DE  NLKDLKRSLR  FAYNITPCDY  ENVEIAFVTT   32
SPE-H   --------  -----NSYN TTNRHNLESL  YKHDSNLIEA  DSIKNSPDIV   34
SEA     SEKSEEINE KDLRKKSELQ GAALGNLKQI YYYNEKAKTE  NKESHDQFLQ   49
                                 α2                β1

SMEZ    HNLVTKKLDV RDARYFFINS EMDEYAANDF KDGDKIAMYS VPFDWNYLSE   80
SMEZ-2  HNLVTKKLDV RDARYFFINS EMDEYAANDF KTGDKIAVYS VPFDWNYLSK   80
SPE-J   ---------- ---------- ---------- ---------- LP....YIFT    6
SPE-C   HTLNIDTQKY RG.KYYISS  EMSYEASQRF KRIDVDVFG  LF....YILN   79
SpeG    NSIHINTKQK RSECILYVDS IVSLGITDQF IKGDKVDVFG LP....YNFS   78
SpeH    TS.HML..KY .SVKKNLSV  FFEKDWISQE FRDKEVDIYA DSAQEVCE..   78
SEA     HTILFKGFFT NHSWYNDLLV DFDSKDIVDK YKGKKVDLYG AYYGYQCAGG   99
         β2           β3     α3    β4

SMEZ    GKVIAY.TYG GMTPYQEE.. PMSKNIDVNL WINRRQIPVP YNQISTNKTT  127
SMEZ-2  GKVTAY.TYG GITPYQKT.. SIPKNIDVNL WINGKQISVE YNEISTNKTT  127
SPE-J   RYDVYY.IYG GVTPSVNSN. SENSKIVGNL LDLGVQQKTL DNPIKIDKPI   54
SPE-C   SHTGEY.IYG GITPAQN.N. KVNHKLLGNL FISGESQQNL NKKILEKDI   126
SPE-G   PPYVDN.IYG GIVKHSNQG. NKSLQFVGIL NQDGKETYLF SEAVRIKKKQ  126
SPE-H   CPGKRYEAFG GILTNSEK. .KEIKVPVNV WDKSKQQ..P PMFITVNKPK  124
SEA     TPNKTACMYG GVTLHDNNRL TEERKVGINL WLDGKQNTVP LETVKTNKKN  149
            β5           β6         β7        β8

SMEZ    VTAQEIDLKV RKFLISQHQL YSSGSSYNSG RLVFHGNDNS DKYSLDLFYV  177
SMEZ-2  VTAQEIDLKV RKFLIAQHQL YSSGSSYNSG RLVFHGNDNS DKYSFDLFYV  177
SPE-J   ETIQEPDFKI RQYLMQTYKI YDPKSPYIKG QLEIAINGNK .HESFNLYDA  103
SPE-C   VTFQEILKI RKYLMDNYKI YDATSPYVSG RIEIGKDGK .HEQIDLSDS   175
SPE-G   ETLQEPDFKI RKFLMEKYNI YDSPSAYISG SLFLATKDSK .HYEVDLKNK  175
SPE-H   VTAQEVDIKV RKLLIKKYDI YNNR..EQKY SKGTVGLDLN SGKDIVFDLY  172
SEA     VTVQELDLQA RRYLQERYNL YNSDVFDGKV QRGLIVFHTS TEPSVNYDLF  199
          β8   α4                β9         β10

SMEZ    ..GYRDKESI FKVYKDNKSF NIDKIGHLDI EIDS  209
SMEZ-2  ..GYRDKESI FKVYKDNKSF NIDKIGHLDI EIDS  209
SPE-J   TSS.STRSDI FKMYKDNKTI NMKDFSHFDI YDWTK 137
SPE-C   PNE.GTRSDI FAKYKDNRII NMKNFSHFDI YLEK  208
SPE-G   DDKLLSRDSF FKRYKDNKIF NSEEISHFDI YLKTH 210
SPE-H   YFGNGDFNSM LKIYSNNERI DSTQF.HVDV SIS   204
SEA     GAQGQNSNTL LRIYRDNKTI NSENM.HIDI YLYTS 233
              α5       β11      β12
```

SEQUENCE LISTING

<160> NUMBER OF SEQ ID NOS: 25

<210> SEQ ID NO 1
<211> LENGTH: 702
<212> TYPE: DNA
<213> ORGANISM: Streptococcus pyogenes
<220> FEATURE:
<221> NAME/KEY: CDS
<222> LOCATION: (1)..(699)

<400> SEQUENCE: 1

```
atg aaa aaa aca aaa ctt att ttt tct ttt act tca ata ttc att gca        48
Met Lys Lys Thr Lys Leu Ile Phe Ser Phe Thr Ser Ile Phe Ile Ala
 1               5                  10                  15 ata att tct cgt cct gtg ttt gga tta gaa gta gat aat aat tcc ctt        96
Ile Ile Ser Arg Pro Val Phe Gly Leu Glu Val Asp Asn Asn Ser Leu
             20                  25                  30 cta agg aat atc tat agt acg att gta tat gaa tat tca gat ata gta       144
Leu Arg Asn Ile Tyr Ser Thr Ile Val Tyr Glu Tyr Ser Asp Ile Val
         35                  40                  45 att gat ttt aaa acc agt cat aac tta gtg act aag aaa ctt gat gtt       192
Ile Asp Phe Lys Thr Ser His Asn Leu Val Thr Lys Lys Leu Asp Val
     50                  55                  60 aga gat gct aga gat ttc ttt att aac tcc gaa atg gac gaa tat gca       240
Arg Asp Ala Arg Asp Phe Phe Ile Asn Ser Glu Met Asp Glu Tyr Ala
 65                  70                  75                  80 gcc aat gat ttt aaa act gga gat aaa ata gct gtg ttc tcc gtc cca       288
Ala Asn Asp Phe Lys Thr Gly Asp Lys Ile Ala Val Phe Ser Val Pro
```

```
                   85                  90                  95
ttt gat tgg aac tat tta tca aaa gga aaa gtc aca gca tat acc tat      336
Phe Asp Trp Asn Tyr Leu Ser Lys Gly Lys Val Thr Ala Tyr Thr Tyr
            100                 105                 110 ggt gga ata aca ccc tac caa aaa act tca ata cct aaa aat atc cct      384
Gly Gly Ile Thr Pro Tyr Gln Lys Thr Ser Ile Pro Lys Asn Ile Pro
            115                 120                 125 gtt aat tta tgg att aat gga aag cag atc tct gtt cct tac aac gaa      432
Val Asn Leu Trp Ile Asn Gly Lys Gln Ile Ser Val Pro Tyr Asn Glu
    130                 135                 140 ata tca act aac aaa aca aca gtt aca gct caa gaa att gat cta aag      480
Ile Ser Thr Asn Lys Thr Thr Val Thr Ala Gln Glu Ile Asp Leu Lys
145                 150                 155                 160 gtt aga aaa ttt tta ata gca caa cat caa tta tat tct tct ggt tct      528
Val Arg Lys Phe Leu Ile Ala Gln His Gln Leu Tyr Ser Ser Gly Ser
                165                 170                 175 agc tac aaa agt ggt aga ctg gtt ttt cat aca aat gat aat tca gat      576
Ser Tyr Lys Ser Gly Arg Leu Val Phe His Thr Asn Asp Asn Ser Asp
            180                 185                 190 aaa tat tct ttc gat ctt ttc tat gta gga tat aga gat aaa gaa agt      624
Lys Tyr Ser Phe Asp Leu Phe Tyr Val Gly Tyr Arg Asp Lys Glu Ser
        195                 200                 205 atc ttt aaa gta tac aaa gac aat aaa tct ttc aat ata gat aaa att      672
Ile Phe Lys Val Tyr Lys Asp Asn Lys Ser Phe Asn Ile Asp Lys Ile
    210                 215                 220 ggg cat tta gat ata gaa att gac tcc taa                              702
Gly His Leu Asp Ile Glu Ile Asp Ser
225                 230

<210> SEQ ID NO 2
<211> LENGTH: 233
<212> TYPE: PRT
<213> ORGANISM: Streptococcus pyogenes

<400> SEQUENCE: 2

Met Lys Lys Thr Lys Leu Ile Phe Ser Phe Thr Ser Ile Phe Ile Ala
1               5                   10                  15

Ile Ile Ser Arg Pro Val Phe Gly Leu Glu Val Asp Asn Asn Ser Leu
            20                  25                  30

Leu Arg Asn Ile Tyr Ser Thr Ile Val Tyr Glu Tyr Ser Asp Ile Val
        35                  40                  45

Ile Asp Phe Lys Thr Ser His Asn Leu Val Thr Lys Lys Leu Asp Val
    50                  55                  60

Arg Asp Ala Arg Asp Phe Phe Ile Asn Ser Glu Met Asp Glu Tyr Ala
65                  70                  75                  80

Ala Asn Asp Phe Lys Thr Gly Asp Lys Ile Ala Val Phe Ser Val Pro
                85                  90                  95

Phe Asp Trp Asn Tyr Leu Ser Lys Gly Lys Val Thr Ala Tyr Thr Tyr
            100                 105                 110

Gly Gly Ile Thr Pro Tyr Gln Lys Thr Ser Ile Pro Lys Asn Ile Pro
        115                 120                 125

Val Asn Leu Trp Ile Asn Gly Lys Gln Ile Ser Val Pro Tyr Asn Glu
    130                 135                 140

Ile Ser Thr Asn Lys Thr Thr Val Thr Ala Gln Glu Ile Asp Leu Lys
145                 150                 155                 160

Val Arg Lys Phe Leu Ile Ala Gln His Gln Leu Tyr Ser Ser Gly Ser
                165                 170                 175
```

-continued

```
Ser Tyr Lys Ser Gly Arg Leu Val Phe His Thr Asn Asp Asn Ser Asp
        180                 185                 190

Lys Tyr Ser Phe Asp Leu Phe Tyr Val Gly Tyr Arg Asp Lys Glu Ser
        195                 200                 205

Ile Phe Lys Val Tyr Lys Asp Asn Lys Ser Phe Asn Ile Asp Lys Ile
        210                 215                 220

Gly His Leu Asp Ile Glu Ile Asp Ser
225                 230

<210> SEQ ID NO 3
<211> LENGTH: 705
<212> TYPE: DNA
<213> ORGANISM: Streptococcus pyogenes
<220> FEATURE:
<221> NAME/KEY: CDS
<222> LOCATION: (1)..(702)

<400> SEQUENCE: 3 atg aaa aca aac att ttg aca att atc ata tta tca tgt gtt ttt agc     48
Met Lys Thr Asn Ile Leu Thr Ile Ile Ile Leu Ser Cys Val Phe Ser
 1               5                  10                  15 tat gga agt caa tta gct tat gca gat gaa aat tta aaa gat tta aaa     96
Tyr Gly Ser Gln Leu Ala Tyr Ala Asp Glu Asn Leu Lys Asp Leu Lys
            20                  25                  30 aga agt tta aga ttt gcc tat aat att acc cca tgc gat tat gaa aat    144
Arg Ser Leu Arg Phe Ala Tyr Asn Ile Thr Pro Cys Asp Tyr Glu Asn
        35                  40                  45 gta gaa att gca ttt gtt act aca aat agc ata cat att aat act aaa    192
Val Glu Ile Ala Phe Val Thr Thr Asn Ser Ile His Ile Asn Thr Lys
    50                  55                  60 caa aaa aga tcg gaa tgt att ctt tat gtt gat tct att gta tct tta    240
Gln Lys Arg Ser Glu Cys Ile Leu Tyr Val Asp Ser Ile Val Ser Leu
65                  70                  75                  80 ggc att act gat cag ttt ata aaa ggg gat aag gtc gat gtt ttt ggt    288
Gly Ile Thr Asp Gln Phe Ile Lys Gly Asp Lys Val Asp Val Phe Gly
                85                  90                  95 ctc cct tat aat ttt tcc cca cct tat gta gat aat att tat ggt ggt    336
Leu Pro Tyr Asn Phe Ser Pro Pro Tyr Val Asp Asn Ile Tyr Gly Gly
            100                 105                 110 att gta aaa cat tcg aat caa gga aat aaa tca tta cag ttt gta gga    384
Ile Val Lys His Ser Asn Gln Gly Asn Lys Ser Leu Gln Phe Val Gly
        115                 120                 125 att tta aat caa gat ggg aaa gaa act tat ttg ccc tct gag gct gtt    432
Ile Leu Asn Gln Asp Gly Lys Glu Thr Tyr Leu Pro Ser Glu Ala Val
    130                 135                 140 cgc ata aaa aag aaa cag ttt act tta cag gaa ttt gat ttt aaa ata    480
Arg Ile Lys Lys Lys Gln Phe Thr Leu Gln Glu Phe Asp Phe Lys Ile
145                 150                 155                 160 aga aaa ttt cta atg gaa aaa tac aat atc tat gat tcg gaa tcg cgt    528
Arg Lys Phe Leu Met Glu Lys Tyr Asn Ile Tyr Asp Ser Glu Ser Arg
                165                 170                 175 tat aca tcg ggg agc ctt ttc ctt gct act aaa gat agt aaa cat tat    576
Tyr Thr Ser Gly Ser Leu Phe Leu Ala Thr Lys Asp Ser Lys His Tyr
            180                 185                 190 gaa gtt gat tta ttt aat aag gat gat aag ctt tta agt cga gac agt    624
Glu Val Asp Leu Phe Asn Lys Asp Asp Lys Leu Leu Ser Arg Asp Ser
        195                 200                 205 ttc ttt aaa agg tat aaa gat aat aag att ttt aat agt gaa gaa att    672
Phe Phe Lys Arg Tyr Lys Asp Asn Lys Ile Phe Asn Ser Glu Glu Ile
210                 215                 220
```

-continued

```
agt cat ttt gat atc tac tta aaa acg cac tag                    705
Ser His Phe Asp Ile Tyr Leu Lys Thr His
225                 230
```

<210> SEQ ID NO 4
<211> LENGTH: 234
<212> TYPE: PRT
<213> ORGANISM: Streptococcus pyogenes

<400> SEQUENCE: 4

```
Met Lys Thr Asn Ile Leu Thr Ile Ile Leu Ser Cys Val Phe Ser
1               5                   10                  15

Tyr Gly Ser Gln Leu Ala Tyr Ala Asp Glu Asn Leu Lys Asp Leu Lys
            20                  25                  30

Arg Ser Leu Arg Phe Ala Tyr Asn Ile Thr Pro Cys Asp Tyr Glu Asn
        35                  40                  45

Val Glu Ile Ala Phe Val Thr Thr Asn Ser Ile His Ile Asn Thr Lys
    50                  55                  60

Gln Lys Arg Ser Glu Cys Ile Leu Tyr Val Asp Ser Ile Val Ser Leu
65                  70                  75                  80

Gly Ile Thr Asp Gln Phe Ile Lys Gly Asp Lys Val Asp Val Phe Gly
                85                  90                  95

Leu Pro Tyr Asn Phe Ser Pro Pro Tyr Val Asp Asn Ile Tyr Gly Gly
            100                 105                 110

Ile Val Lys His Ser Asn Gln Gly Asn Lys Ser Leu Gln Phe Val Gly
        115                 120                 125

Ile Leu Asn Gln Asp Gly Lys Glu Thr Tyr Leu Pro Ser Glu Ala Val
    130                 135                 140

Arg Ile Lys Lys Lys Gln Phe Thr Leu Gln Glu Phe Asp Phe Lys Ile
145                 150                 155                 160

Arg Lys Phe Leu Met Glu Lys Tyr Asn Ile Tyr Asp Ser Glu Ser Arg
                165                 170                 175

Tyr Thr Ser Gly Ser Leu Phe Leu Ala Thr Lys Asp Ser Lys His Tyr
            180                 185                 190

Glu Val Asp Leu Phe Asn Lys Asp Asp Lys Leu Leu Ser Arg Asp Ser
        195                 200                 205

Phe Phe Lys Arg Tyr Lys Asp Asn Lys Ile Phe Asn Ser Glu Glu Ile
    210                 215                 220

Ser His Phe Asp Ile Tyr Leu Lys Thr His
225                 230
```

<210> SEQ ID NO 5
<211> LENGTH: 711
<212> TYPE: DNA
<213> ORGANISM: Streptococcus pyogenes
<220> FEATURE:
<221> NAME/KEY: CDS
<222> LOCATION: (1)..(708)

<400> SEQUENCE: 5

```
atg aga tat aat tgt cgc tac tca cat att gat aag aaa atc tac agc     48
Met Arg Tyr Asn Cys Arg Tyr Ser His Ile Asp Lys Lys Ile Tyr Ser
1               5                   10                  15 atg att ata tgt ttg tca ttt ctt tta tat tcc aat gtt gtt caa gca     96
Met Ile Ile Cys Leu Ser Phe Leu Leu Tyr Ser Asn Val Val Gln Ala
            20                  25                  30 aat tct tat aat aca acc aat aga cat aat cta gaa tcg ctt tat aag    144
Asn Ser Tyr Asn Thr Thr Asn Arg His Asn Leu Glu Ser Leu Tyr Lys
        35                  40                  45
```

```
cat gat tct aac ttg att gaa gcc gat agt ata aaa aat tct cca gat      192
His Asp Ser Asn Leu Ile Glu Ala Asp Ser Ile Lys Asn Ser Pro Asp
 50                  55                  60 att gta aca agc cat atg ttg aaa tat agt gtc aag gat aaa aat ttg      240
Ile Val Thr Ser His Met Leu Lys Tyr Ser Val Lys Asp Lys Asn Leu
 65                  70                  75                  80 tca gtt ttt ttt gag aaa gat tgg ata tca cag gaa ttc aaa gat aaa      288
Ser Val Phe Phe Glu Lys Asp Trp Ile Ser Gln Glu Phe Lys Asp Lys
                 85                  90                  95 gaa gta gat att tat gct cta tct gca caa gag gtt tgt gaa tgt cca      336
Glu Val Asp Ile Tyr Ala Leu Ser Ala Gln Glu Val Cys Glu Cys Pro
            100                 105                 110 ggg aaa agg tat gaa gcg ttt ggt gga att aca tta act aat tca gaa      384
Gly Lys Arg Tyr Glu Ala Phe Gly Gly Ile Thr Leu Thr Asn Ser Glu
        115                 120                 125 aaa aaa gaa att aaa gtt cct gta aac gtg tgg gat aaa agt aaa caa      432
Lys Lys Glu Ile Lys Val Pro Val Asn Val Trp Asp Lys Ser Lys Gln
130                 135                 140 cag ccg cct atg ttt att aca gtc aat aaa ccg aaa gta acc gct cag      480
Gln Pro Pro Met Phe Ile Thr Val Asn Lys Pro Lys Val Thr Ala Gln
145                 150                 155                 160 gaa gtg gat ata aaa gtt aga aag tta ttg att aag aaa tac gat atc      528
Glu Val Asp Ile Lys Val Arg Lys Leu Leu Ile Lys Lys Tyr Asp Ile
                165                 170                 175 tat aat aac cgg gaa caa aaa tac tct aaa gga act gtt acc tta gat      576
Tyr Asn Asn Arg Glu Gln Lys Tyr Ser Lys Gly Thr Val Thr Leu Asp
            180                 185                 190 tta aat tca ggt aaa gat att gtt ttt gat ttg tat tat ttt ggc aat      624
Leu Asn Ser Gly Lys Asp Ile Val Phe Asp Leu Tyr Tyr Phe Gly Asn
        195                 200                 205 gga gac ttt aat agc atg cta aaa ata tat tcc aat aac gag aga ata      672
Gly Asp Phe Asn Ser Met Leu Lys Ile Tyr Ser Asn Asn Glu Arg Ile
210                 215                 220 gac tca act caa ttt cat gta gat gtg tca atc agc taa                  711
Asp Ser Thr Gln Phe His Val Asp Val Ser Ile Ser
225                 230                 235

<210> SEQ ID NO 6
<211> LENGTH: 236
<212> TYPE: PRT
<213> ORGANISM: Streptococcus pyogenes

<400> SEQUENCE: 6

Met Arg Tyr Asn Cys Arg Tyr Ser His Ile Asp Lys Lys Ile Tyr Ser
 1               5                  10                  15

Met Ile Ile Cys Leu Ser Phe Leu Leu Tyr Ser Asn Val Val Gln Ala
             20                  25                  30

Asn Ser Tyr Asn Thr Thr Asn Arg His Asn Leu Glu Ser Leu Tyr Lys
         35                  40                  45

His Asp Ser Asn Leu Ile Glu Ala Asp Ser Ile Lys Asn Ser Pro Asp
     50                  55                  60

Ile Val Thr Ser His Met Leu Lys Tyr Ser Val Lys Asp Lys Asn Leu
 65                  70                  75                  80

Ser Val Phe Phe Glu Lys Asp Trp Ile Ser Gln Glu Phe Lys Asp Lys
                 85                  90                  95

Glu Val Asp Ile Tyr Ala Leu Ser Ala Gln Glu Val Cys Glu Cys Pro
            100                 105                 110

Gly Lys Arg Tyr Glu Ala Phe Gly Gly Ile Thr Leu Thr Asn Ser Glu
```

```
                115                 120                 125
Lys Lys Glu Ile Lys Val Pro Val Asn Val Trp Asp Lys Ser Lys Gln
    130                 135                 140

Gln Pro Pro Met Phe Ile Thr Val Asn Lys Pro Lys Val Thr Ala Gln
145                 150                 155                 160

Glu Val Asp Ile Lys Val Arg Lys Leu Leu Ile Lys Lys Tyr Asp Ile
                165                 170                 175

Tyr Asn Asn Arg Glu Gln Lys Tyr Ser Lys Gly Thr Val Thr Leu Asp
            180                 185                 190

Leu Asn Ser Gly Lys Asp Ile Val Phe Asp Leu Tyr Tyr Phe Gly Asn
        195                 200                 205

Gly Asp Phe Asn Ser Met Leu Lys Ile Tyr Ser Asn Asn Glu Arg Ile
    210                 215                 220

Asp Ser Thr Gln Phe His Val Asp Val Ser Ile Ser
225                 230                 235

<210> SEQ ID NO 7
<211> LENGTH: 414
<212> TYPE: DNA
<213> ORGANISM: Streptococcus pyogenes
<220> FEATURE:
<221> NAME/KEY: CDS
<222> LOCATION: (1)..(411)

<400> SEQUENCE: 7 ctt ccg tac ata ttt act cgt tat gat gtt tat tat ata tat ggt ggg      48
Leu Pro Tyr Ile Phe Thr Arg Tyr Asp Val Tyr Tyr Ile Tyr Gly Gly
  1               5                  10                  15 gtt aca cca tca gta aac agt aat tcg gaa aat agt aaa att gta ggt      96
Val Thr Pro Ser Val Asn Ser Asn Ser Glu Asn Ser Lys Ile Val Gly
             20                  25                  30 aat tta cta ata gat gga gtc cag caa aaa aca cta ata aat ccc ata     144
Asn Leu Leu Ile Asp Gly Val Gln Gln Lys Thr Leu Ile Asn Pro Ile
         35                  40                  45 aaa ata gat aaa cct att ttt acg att caa gaa ttt gac ttc aaa atc     192
Lys Ile Asp Lys Pro Ile Phe Thr Ile Gln Glu Phe Asp Phe Lys Ile
     50                  55                  60 aga caa tat ctt atg caa aca tac aaa att tat gat cct aat tct cca     240
Arg Gln Tyr Leu Met Gln Thr Tyr Lys Ile Tyr Asp Pro Asn Ser Pro
 65                  70                  75                  80 tac ata aaa ggg caa tta gaa att gcg atc aat ggc aat aaa cat gaa     288
Tyr Ile Lys Gly Gln Leu Glu Ile Ala Ile Asn Gly Asn Lys His Glu
                 85                  90                  95 agt ttt aac tta tat gat gca acc tca tct agt aca agg agt gat att     336
Ser Phe Asn Leu Tyr Asp Ala Thr Ser Ser Ser Thr Arg Ser Asp Ile
            100                 105                 110 ttt aaa aaa tat aaa gac aat aag act ata aat atg aaa gat ttc agc     384
Phe Lys Lys Tyr Lys Asp Asn Lys Thr Ile Asn Met Lys Asp Phe Ser
        115                 120                 125 cat ttt gat att tac ctt tgg act aaa taa                             414
His Phe Asp Ile Tyr Leu Trp Thr Lys
    130                 135

<210> SEQ ID NO 8
<211> LENGTH: 137
<212> TYPE: PRT
<213> ORGANISM: Streptococcus pyogenes

<400> SEQUENCE: 8

Leu Pro Tyr Ile Phe Thr Arg Tyr Asp Val Tyr Tyr Ile Tyr Gly Gly
```

```
                1               5              10              15
        Val Thr Pro Ser Val Asn Ser Asn Ser Glu Asn Ser Lys Ile Val Gly
                        20                  25                  30

Asn Leu Leu Ile Asp Gly Val Gln Gln Lys Thr Leu Ile Asn Pro Ile
                    35                  40                  45

Lys Ile Asp Lys Pro Ile Phe Thr Ile Gln Glu Phe Asp Phe Lys Ile
                    50                  55                  60

Arg Gln Tyr Leu Met Gln Thr Tyr Lys Ile Tyr Asp Pro Asn Ser Pro
         65                  70                  75                  80

Tyr Ile Lys Gly Gln Leu Glu Ile Ala Ile Asn Gly Asn Lys His Glu
                        85                  90                  95

Ser Phe Asn Leu Tyr Asp Ala Thr Ser Ser Ser Thr Arg Ser Asp Ile
                        100                 105                 110

Phe Lys Lys Tyr Lys Asp Asn Lys Thr Ile Asn Met Lys Asp Phe Ser
                        115                 120                 125

His Phe Asp Ile Tyr Leu Trp Thr Lys
                        130                 135

<210> SEQ ID NO 9
<211> LENGTH: 204
<212> TYPE: PRT
<213> ORGANISM: Streptococcus pyogenes

<400> SEQUENCE: 9

Leu Glu Val Asp Asn Asn Ser Leu Leu Arg Asn Ile Tyr Ser Thr Ile
         1               5                  10                  15

Val Tyr Glu Tyr Ser Asp Thr Val Ile Asp Phe Lys Thr Ser His Asn
                        20                  25                  30

Leu Val Thr Lys Lys Leu Asp Val Arg Asp Ala Arg Asp Phe Phe Ile
                    35                  40                  45

Asn Ser Glu Met Asp Glu Tyr Ala Ala Asn Asp Phe Lys Asp Gly Asp
                    50                  55                  60

Lys Ile Ala Met Phe Ser Val Pro Phe Asp Trp Asn Tyr Leu Ser Glu
         65                  70                  75                  80

Gly Lys Val Ile Ala Tyr Thr Tyr Gly Met Thr Pro Tyr Gln Glu Glu
                        85                  90                  95

Pro Met Ser Lys Asn Ile Pro Val Leu Trp Ile Asn Arg Arg Gln Ile
                        100                 105                 110

Pro Val Pro Tyr Asn Gln Ile Ser Thr Asn Lys Thr Thr Val Thr Ala
                        115                 120                 125

Gln Glu Ile Asp Leu Lys Val Lys Phe Leu Ile Ser Gln His Gln Leu
                    130                 135                 140

Ser Ser Gly Ser Ser Tyr Lys Ser Gly Lys Leu Val Phe His Thr Asn
        145                 150                 155                 160

Asp Asn Ser Asp Lys Tyr Ser Leu Asp Leu Phe Tyr Val Gly Tyr Arg
                        165                 170                 175

Asp Lys Glu Ser Ile Phe Lys Val Tyr Lys Asp Lys Ser Phe Asn Ile
                        180                 185                 190

Asp Lys Ile Gly His Leu Asp Ile Glu Ile Asp Ser
                        195                 200

<210> SEQ ID NO 10
<211> LENGTH: 203
<212> TYPE: PRT
<213> ORGANISM: Streptococcus pyogenes
```

<400> SEQUENCE: 10

```
Asp Ser Lys Lys Asp Ile Ser Asn Val Lys Ser Asp Leu Leu Tyr Ala
1               5                   10                  15

Tyr Thr Ile Thr Pro Tyr Asp Tyr Lys Asp Cys Arg Val Asn Phe Ser
            20                  25                  30

Thr Thr His Thr Leu Asn Ile Asp Thr Gln Lys Tyr Arg Gly Lys Asp
        35                  40                  45

Tyr Tyr Ile Ser Ser Glu Met Ser Tyr Glu Ala Ser Gln Lys Phe Lys
    50                  55                  60

Arg Asp Asp His Val Asp Val Phe Gly Leu Phe Tyr Ile Leu Asn Ser
65                  70                  75                  80

His Thr Gly Glu Tyr Ile Tyr Gly Ile Thr Pro Ala Gln Asn Asn Lys
                85                  90                  95

Val Asn His Lys Leu Leu Gly Leu Phe Ile Ser Gly Glu Ser Gln Gln
            100                 105                 110

Asn Leu Asn Asn Lys Ile Ile Leu Glu Lys Asp Ile Val Thr Phe Gln
        115                 120                 125

Glu Ile Asp Phe Lys Ile Lys Tyr Leu Met Asp Asn Tyr Lys Ile Asp
    130                 135                 140

Ala Thr Ser Pro Tyr Val Ser Gly Arg Ile Glu Ile Gly Thr Lys Asp
145                 150                 155                 160

Gly Lys His Glu Gln Ile Asp Leu Phe Asp Ser Pro Asn Glu Gly Thr
                165                 170                 175

Arg Ser Asp Ile Phe Ala Lys Tyr Lys Asp Arg Ile Ile Asn Met Lys
            180                 185                 190

Asn Phe Ser His Phe Asp Ile Tyr Leu Glu Lys
        195                 200
```

<210> SEQ ID NO 11
<211> LENGTH: 227
<212> TYPE: PRT
<213> ORGANISM: Streptococcus aureus

<400> SEQUENCE: 11

```
Ser Glu Lys Ser Glu Glu Ile Asn Glu Lys Asp Leu Arg Lys Lys Ser
1               5                   10                  15

Glu Leu Gln Gly Ala Ala Leu Gly Asn Lys Gln Ile Tyr Tyr Tyr Asn
            20                  25                  30

Glu Lys Ala Lys Thr Glu Asn Lys Glu Ser His Asp Gln Phe Leu Gln
        35                  40                  45

His Thr Ile Leu Phe Lys Gly Phe Phe Thr Asn His Ser Trp Tyr Asn
    50                  55                  60

Asp Leu Leu Val Asp Phe Asp Ser Lys Asp Ile Val Asp Lys Tyr Lys
65                  70                  75                  80

Gly Lys Lys Val Asp Leu Tyr Gly Ala Tyr Tyr Gly Tyr Gln Cys Ala
                85                  90                  95

Gly Gly Thr Pro Asn Lys Thr Ala Cys Met Tyr Gly Val Thr Leu His
            100                 105                 110

Asp Asn Asn Arg Leu Thr Glu Glu Lys Lys Val Pro Ile Asn Leu Trp
        115                 120                 125

Leu Asp Lys Gln Asn Thr Val Pro Leu Glu Thr Val Lys Thr Asn Lys
    130                 135                 140

Lys Asn Val Thr Val Gln Glu Leu Asp Leu Gln Ala Arg Tyr Leu Gln
145                 150                 155                 160
```

-continued

```
Glu Lys Tyr Asn Leu Asn Ser Asp Val Phe Asp Gly Lys Val Gln Arg
            165                 170                 175

Gly Leu Ile Val Phe His Thr Ser Thr Glu Pro Ser Val Asn Tyr Asp
        180                 185                 190

Leu Phe Gly Ala Gln Gly Gln Asn Ser Asn Thr Leu Leu Arg Ile Tyr
    195                 200                 205

Arg Asp Lys Thr Ile Asn Ser Glu Asn Met His Ile Asp Ile Tyr Leu
210                 215                 220

Tyr Thr Ser
225

<210> SEQ ID NO 12
<211> LENGTH: 24
<212> TYPE: DNA
<213> ORGANISM: Artificial Sequence
<220> FEATURE:
<223> OTHER INFORMATION: Primer

<400> SEQUENCE: 12
tgggatcctt agaagtagat aata                                    24

<210> SEQ ID NO 13
<211> LENGTH: 23
<212> TYPE: DNA
<213> ORGANISM: Artificial Sequence
<220> FEATURE:
<223> OTHER INFORMATION: Primer

<400> SEQUENCE: 13
aagaattctt aggagtcaat ttc                                     23

<210> SEQ ID NO 14
<211> LENGTH: 30
<212> TYPE: DNA
<213> ORGANISM: Artificial Sequence
<220> FEATURE:
<223> OTHER INFORMATION: Primer

<400> SEQUENCE: 14
ctggatccga tgaaaattta aaagatttaa                              30

<210> SEQ ID NO 15
<211> LENGTH: 21
<212> TYPE: DNA
<213> ORGANISM: Artificial Sequence
<220> FEATURE:
<223> OTHER INFORMATION: Primer

<400> SEQUENCE: 15
aagaattcgg ggggagaata g                                       21

<210> SEQ ID NO 16
<211> LENGTH: 26
<212> TYPE: DNA
<213> ORGANISM: Artificial Sequence
<220> FEATURE:
<223> OTHER INFORMATION: Primer

<400> SEQUENCE: 16
ttggatccaa ttcttataat acaacc                                  26

<210> SEQ ID NO 17
<211> LENGTH: 23
<212> TYPE: DNA
```

-continued

```
<213> ORGANISM: Artificial Sequence
<220> FEATURE:
<223> OTHER INFORMATION: Primer

<400> SEQUENCE: 17
aaaagctttt agctgattga cac                                              23

<210> SEQ ID NO 18
<211> LENGTH: 20
<212> TYPE: DNA
<213> ORGANISM: Artificial Sequence
<220> FEATURE:
<223> OTHER INFORMATION: Primer

<400> SEQUENCE: 18
gctatttcgg agagaaccag                                                  20

<210> SEQ ID NO 19
<211> LENGTH: 20
<212> TYPE: DNA
<213> ORGANISM: Artificial Sequence
<220> FEATURE:
<223> OTHER INFORMATION: Primer

<400> SEQUENCE: 19
ctgaaacatc taagtagctg                                                  20

<210> SEQ ID NO 20
<211> LENGTH: 204
<212> TYPE: PRT
<213> ORGANISM: Streptococcus pyogenes

<400> SEQUENCE: 20

Leu Glu Val Asp Asn Asn Ser Leu Leu Arg Asn Ile Tyr Ser Thr Ile
  1               5                  10                  15

Val Tyr Glu Tyr Ser Asp Thr Val Ile Asp Phe Lys Thr Ser His Asn
             20                  25                  30

Leu Val Thr Lys Lys Leu Asp Val Arg Asp Ala Arg Asp Phe Phe Ile
         35                  40                  45

Asn Ser Glu Met Asp Glu Tyr Ala Ala Asn Asp Phe Lys Thr Gly Asp
     50                  55                  60

Lys Ile Ala Val Phe Ser Val Pro Phe Asp Trp Asn Tyr Leu Ser Lys
 65                  70                  75                  80

Gly Lys Val Thr Ala Tyr Thr Tyr Gly Thr Thr Pro Tyr Gln Lys Thr
                 85                  90                  95

Ser Ile Leu Lys Asn Ile Pro Val Leu Trp Ile Asn Gly Lys Gln Ile
            100                 105                 110

Pro Val Pro Tyr Asn Glu Ile Ser Thr Asn Lys Thr Thr Val Thr Ala
        115                 120                 125

Gln Glu Ile Asp Leu Lys Val Lys Phe Leu Ile Ala Gln His Gln Leu
    130                 135                 140

Ser Ser Gly Ser Ser Tyr Lys Ser Gly Arg Leu Val Phe His Thr Asn
145                 150                 155                 160

Asp Asn Ser Asp Lys Tyr Ser Phe Asp Leu Phe Tyr Val Gly Tyr Arg
                165                 170                 175

Asp Lys Glu Ser Ile Phe Lys Val Tyr Lys Asp Lys Ser Phe Asn Ile
            180                 185                 190

Asp Lys Ile Gly His Leu Asp Ile Glu Ile Asp Ser
        195                 200
```

<210> SEQ ID NO 21
<211> LENGTH: 206
<212> TYPE: PRT
<213> ORGANISM: Streptococcus pyogenes

<400> SEQUENCE: 21

Asp Glu Asn Leu Lys Asp Leu Lys Arg Ser Leu Arg Phe Ala Tyr Asn
 1               5                  10                  15

Ile Thr Pro Cys Asp Tyr Glu Asn Val Glu Ile Ala Phe Val Thr Thr
            20                  25                  30

Asn Ser Ile His Ile Asn Thr Lys Gln Lys Arg Ser Glu Cys Ile Leu
        35                  40                  45

Tyr Val Asp Ser Ile Val Ser Leu Gly Ile Thr Asp Gln Phe Ile Lys
    50                  55                  60

Gly Asp Lys Val Asp Val Phe Gly Leu Pro Tyr Asn Phe Ser Pro Pro
65                  70                  75                  80

Tyr Val Asp Asn Ile Tyr Gly Ile Val Lys His Ser Asn Gln Gly Asn
                85                  90                  95

Lys Ser Leu Gln Phe Val Gly Ile Leu Asn Gln Asp Gly Lys Glu Thr
            100                 105                 110

Tyr Leu Pro Ser Glu Ala Val Arg Ile Lys Lys Lys Gln Phe Thr Leu
        115                 120                 125

Gln Glu Phe Asp Phe Lys Ile Lys Phe Leu Met Glu Lys Tyr Asn Ile
    130                 135                 140

Asp Ser Glu Ser Arg Tyr Thr Ser Gly Ser Leu Phe Leu Ala Thr Lys
145                 150                 155                 160

Asp Ser Lys His Tyr Glu Val Asp Leu Phe Asn Lys Asp Asp Lys Leu
                165                 170                 175

Leu Ser Arg Asp Ser Phe Phe Lys Arg Tyr Lys Asp Lys Ile Phe Asn
            180                 185                 190

Ser Glu Glu Ile Ser His Phe Asp Ile Tyr Leu Lys Thr His
        195                 200                 205

<210> SEQ ID NO 22
<211> LENGTH: 204
<212> TYPE: PRT
<213> ORGANISM: Streptococcus pyogenes

<400> SEQUENCE: 22

Asn Ser Tyr Asn Thr Thr Asn Arg His Asn Leu Glu Ser Leu Tyr Lys
 1               5                  10                  15

His Asp Ser Asn Leu Ile Glu Ala Asp Ser Ile Lys Asn Ser Pro Asp
            20                  25                  30

Ile Val Thr Ser His Met Leu Lys Tyr Ser Val Lys Asp Lys Asn Leu
        35                  40                  45

Ser Val Phe Phe Glu Lys Asp Trp Ile Ser Gln Glu Phe Lys Asp Lys
    50                  55                  60

Glu Val Asp Ile Tyr Ala Leu Ser Ala Gln Glu Val Cys Glu Cys Pro
65                  70                  75                  80

Gly Lys Arg Tyr Glu Ala Phe Gly Gly Ile Thr Leu Thr Asn Ser Glu
                85                  90                  95

Lys Lys Glu Ile Lys Val Pro Val Asn Val Trp Asp Lys Ser Lys Gln
            100                 105                 110

Gln Pro Pro Met Phe Ile Thr Val Asn Lys Pro Lys Val Thr Ala Gln
        115                 120                 125

```
Glu Val Asp Ile Lys Val Arg Lys Leu Leu Ile Lys Lys Tyr Asp Ile
    130                 135                 140
Tyr Asn Asn Arg Glu Gln Lys Tyr Ser Lys Gly Thr Val Thr Leu Asp
145                 150                 155                 160
Leu Asn Ser Gly Lys Asp Ile Val Phe Asp Leu Tyr Tyr Phe Gly Asn
                165                 170                 175
Gly Asp Phe Asn Ser Met Leu Lys Ile Tyr Ser Asn Asn Glu Arg Ile
            180                 185                 190
Asp Ser Thr Gln Phe His Val Asp Val Ser Ile Ser
        195                 200

<210> SEQ ID NO 23
<211> LENGTH: 5
<212> TYPE: PRT
<213> ORGANISM: Streptococcus pyogenes

<400> SEQUENCE: 23

Glu Glu Pro Met Ser
1               5

<210> SEQ ID NO 24
<211> LENGTH: 5
<212> TYPE: PRT
<213> ORGANISM: Streptococcus pyogenes

<400> SEQUENCE: 24

Lys Thr Ser Ile Leu
1               5

<210> SEQ ID NO 25
<211> LENGTH: 5
<212> TYPE: PRT
<213> ORGANISM: Streptococcus pyogenes

<400> SEQUENCE: 25

Lys Thr Ser Ile Pro
1               5
```